(12) United States Patent
Hoffman et al.

(10) Patent No.: US 10,112,902 B2
(45) Date of Patent: Oct. 30, 2018

(54) FUNGICIDAL PYRIDYLAMIDINES

(71) Applicant: SYNGENTA PARTICIPATIONS AG, Basel (CH)

(72) Inventors: Thomas James Hoffman, Stein (CH); Sarah Sulzer-Mosse, Stine (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/524,534

(22) PCT Filed: Oct. 30, 2015

(86) PCT No.: PCT/EP2015/075312
§ 371 (c)(1),
(2) Date: May 4, 2017

(87) PCT Pub. No.: WO2016/071239
PCT Pub. Date: May 12, 2016

(65) Prior Publication Data
US 2017/0313660 A1    Nov. 2, 2017

(30) Foreign Application Priority Data

Nov. 6, 2014 (EP) .................................... 14191976

(51) Int. Cl.
| | | |
|---|---|---|
| *C07D 213/85* | (2006.01) | |
| *A01N 43/40* | (2006.01) | |
| *C07D 213/75* | (2006.01) | |
| *C07D 213/74* | (2006.01) | |

(52) U.S. Cl.
CPC ............ *C07D 213/85* (2013.01); *A01N 43/40* (2013.01); *C07D 213/74* (2013.01); *C07D 213/75* (2013.01)

(58) Field of Classification Search
None
See application file for complete search history.

(56) References Cited

FOREIGN PATENT DOCUMENTS

WO    2012146125 A1    11/2012

OTHER PUBLICATIONS

International Search Report dated Dec. 11, 2015 of PCT/EP2015/075312 filed Oct. 30, 2015.

*Primary Examiner* — Heidi Reese
(74) *Attorney, Agent, or Firm* — James Cueva

(57) ABSTRACT

The invention relates to compounds of formula (I) wherein $R^1$, $R^2$, $R^3$, $R^4$, $R^5$, $R^6$, $R^7$, $R^8$, $R^9$ and $R^{10}$ are as defined in the claims. The invention further provides compositions which comprise these compounds and to their use in agriculture or horticulture for controlling or preventing infestation of plants by phytopathogenic microorganisms, preferably fungi.

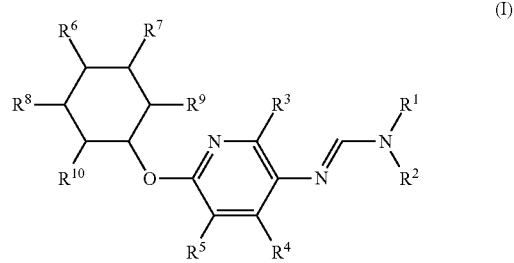

11 Claims, No Drawings

FUNGICIDAL PYRIDYLAMIDINES

RELATED APPLICATION INFORMATION

This application is a 371 of International Application No. PCT/US2015/075312, filed Oct. 30, 2015 which claims priority to EP Application No. 14191976.1 filed Nov. 6, 2014, the contents of which are incorporated herein by reference herein.

The present invention relates to novel microbiocidal, in particular fungicidal, pyridylamidine compounds. It further relates to intermediates used in the preparation of these compounds, to compositions which comprise these compounds, and to their use in agriculture or horticulture for controlling or preventing infestation of plants by phytopathogenic microorganisms, preferably fungi.

Certain pyridylamidines derivatives have been proposed in the literature as microbiocidal active ingredients in pesticides. For example, WO 00/46184, WO 03/093224 and WO 12/146125 disclose pyridylamidines which are useful as fungicides. However, the biological properties of these known compounds are not entirely satisfactory for controlling or preventing infestation of plants by phytopathogenic microorganisms, which is why there is a need to provide other compounds which have microbicidal properties.

The present invention relates to compounds of formula (I)

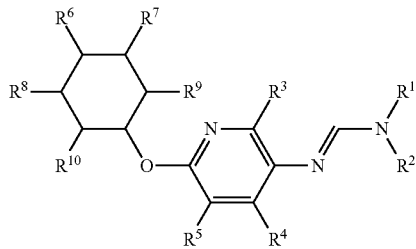

wherein $R^1$ and $R^2$ independently represent hydrogen, $C_1$-$C_4$alkyl, $C_1$-$C_4$fluoroalkyl or $C_3$-$C_6$cycloalkyl; or $R^1$ and $R^2$ together with the nitrogen atom to which they are attached form a three to six-membered saturated cyclic group which may optionally contain one oxygen or one sulphur atom;

$R^3$ represents fluorine, chlorine, bromine, $C_1$-$C_4$ alkyl, $C_2$-$C_4$ alkenyl, $C_1$-$C_4$ haloalkyl, $C_1$-$C_4$ alkoxy or $C_3$-$C_6$ cycloalkyl;

$R^4$ represents hydrogen, halogen, cyano, hydroxy, formyl, carboxy, amino, $C_1$-$C_4$ alkyl, $C_2$-$C_6$ alkenyl, $C_2$-$C_6$ alkynl, $C_1$-$C_6$ haloalkyl, $C_1$-$C_6$ alkoxy or $C_3$-$C_6$ cycloalkyl;

$R^5$ represents hydrogen, halogen, cyano, $C_1$-$C_4$ alkyl, $C_1$-$C_4$ haloalkyl, $C_2$-$C_4$ alkynyl, $C_1$-$C_4$ alkoxy or $C_3$-$C_6$ cycloalkyl;

$R^6$, $R^7$, $R^8$, $R^9$ and $R^{10}$ independently represent hydrogen or $C_1$-$C_6$ fluoroalkoxy;

wherein at least one of $R^6$, $R^7$, $R^8$, $R^9$ and $R^{10}$ represent $C_1$-$C_6$ fluoroalkoxy;

and tautomers/isomers/enantiomers/salts and N-oxides of these compounds.

Substituents at a nitrogen atom are always different from halogen. A hydroxy, mercapto or amino substituent is not to be placed on an α-carbon relative to a heteroatom of a core fragment.

Halogen, either as a lone substituent or in combination with another substituent (e.g. haloalkyl) is generally fluorine, chlorine, bromine or iodine, and usually fluorine, chlorine or bromine.

Each alkyl moiety (including the alkyl moiety of alkoxy, alkylthio, etc.) is a straight or branched chain and, depending on the number of carbon atoms it contains, is, for example, methyl, ethyl, n-propyl, n-butyl, n-pentyl, n-hexyl, iso-propyl, sec-butyl, iso-butyl, tert-butyl, neo-pentyl, n-heptyl or 1,3-dimethylbutyl, and usually methyl or ethyl.

The alkenyl and alkynyl groups can be mono- or di-unsaturated and examples thereof are derived from the above mentioned alkyl groups.

The alkenyl group is an unsaturated straight or branched chain having a carbon-carbon double bond and, depending on the number of carbon atoms it contains, is, for example ethenyl, 1-propenyl, 2-propenyl, 1-methyl-ethenyl, 1-butenyl, 2-butenyl, 3-butenyl, 1-methyl-1-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, and usually 2-propenyl, 1-methyl-2-propenyl, 2-butenyl, 2-methyl-2-propenyl.

The alkynyl group is an unsaturated straight or branched chain having a carbon-carbon triple bond and, depending on the number of carbon atoms it contains, is, for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 3,3-dimethyl-1-butynyl, 1-ethyl-2-butynyl, 1,1-dimethyl-2-butynyl, 1-ethyl-3-butynyl, 2-ethyl-3-butynyl, 1,1-dimethyl-3-butynyl, 2,2-dimethyl-3-butynyl, 1,2-dimethyl-3-butynyl.

Haloalkyl moieties are alkyl moieties which are substituted by one or more of the same or different halogen atoms and are, for example, monofluoromethyl, difluoromethyl, trifluoromethyl, monochloromethyl, dichloromethyl, trichloromethyl, 2,2,2-trifluoroethyl, 2,2-difluoroethyl, 2-fluoroethyl, 1,1-difluoroethyl, 1-fluoroethyl, 2-chloroethyl, pentafluoroethyl, 1,1-difluoro-2,2,2-trichloroethyl, 2,2,3,3-tetrafluoroethyl and 2,2,2-trichloroethyl, and typically trichloromethyl, difluorochloromethyl, difluoromethyl, trifluoromethyl and dichlorofluoromethyl.

Alkoxy is, for example, methoxy, ethoxy, propoxy, iso-propoxy, n-butoxy, iso-butoxy, sec-butoxy and tert-butoxy, and usually methoxy or ethoxy.

Haloalkoxy is, for example, fluoromethoxy, difluoromethoxy, trifluoromethoxy, 2,2,2-trifluoroethoxy, 1,1,2,2- tetrafluoroethoxy, 2-fluoroethoxy, 2-chloroethoxy, 2,2-difluoroethoxy and 2,2,2-trichloroethoxy, and usually difluoromethoxy, 2-chloroethoxy and trifluoromethoxy.

Alkylthio is, for example, methylthio, ethylthio, propylthio, iso-propylthio, n-butylthio, iso-butylthio, sec-butylthio or tert-butylthio, and usually methylthio or ethylthio.

Alkylsulphonyl is, for example, methylsulphonyl, ethylsulphonyl, propylsulphonyl, iso-propylsulphonyl, n-butylsulphonyl, iso-butylsulphonyl, sec-butylsulphonyl or tert-butylsulphonyl, and usually methylsulphonyl or ethylsulphonyl.

Alkylsulphinyl is, for example, methylsulphinyl, ethylsulphinyl, propylsulphinyl, iso-propylsulphinyl, n-butylsulphinyl, iso-butylsulphinyl, sec-butylsulphinyl or tert-butylsulphinyl, and usually methylsulphinyl or ethylsulphinyl.

Cycloalkyl may be saturated or partially unsaturated, preferably fully saturated, and is, for example, cyclopropyl, cyclobutyl, cyclopentyl or cyclohexyl.

Alkoxyalkyl is, for example, methoxymethyl, methoxyethyl, ethoxymethyl, ethoxyethyl, n-propoxymethyl, n-propoxyethyl, iso-propoxymethyl or iso-propoxyethyl.

Aryl includes phenyl, naphthyl, anthracyl, fluorenyl and indanyl, but is usually phenyl.

Carbocycle includes cycloalkyl groups and aryl groups.

Heterocycloalkyl is a non-aromatic ring that may be saturated or partially unsaturated, preferably fully saturated, containing carbon atoms as ring members and at least one heteroatom selected from O, S and N as ring members. Examples include oxiranyl, oxetanyl, tetrahydrofuranyl, tetrahydropyranyl, 1,3-dioxolanyl, 1,4-dioxanyl, aziridinyl, azetidinyl, pyrrolidinyl, piperidinyl, oxazinanyl, morpholinyl, thiomorpholinyl, imidazolidinyl, pyrazolidinyl and piperazinyl, preferably morpholinyl, pyrrolidinyl, piperdinyl and piperazinyl, more preferably morpholinyl and pyrollidinyl.

Heteroaryl is, for example, a monovalent monocyclic or bicyclic aromatic hydrocarbon radical. Examples of monocyclic groups include pyridyl, pyridazinyl, pyrimidinyl, pyrazinyl, pyrrolyl, pyrazolyl, imidazolyl, triazolyl, tetrazolyl, furanyl, thiophenyl, oxazolyl, isoxazolyl, oxadiazolyl, thiazolyl, isothiazolyl, and thiadiazolyl. Examples of bicyclic groups include quinolinyl, cinnolinyl, quinoxalinyl, benzimidazolyl, benzothiophenyl, and benzothiadiazolyl. Monocyclic heteroaryl groups are preferred, preferably pyridyl, pyrrolyl, imidazolyl and triazolyl, e.g. 1,2,4 triazolyl, pyridyl and imidazolyl being most preferred.

The terms "heterocycle" and "heterocyclic ring" are used interchangeably and are defined to include heterocycloalkyl and heteroaryl groups. Any reference herein to a heterocycle or heterocyclic ring preferably refers to the specific examples given under the definition of heteroaryl and heterocycloalkyl above, and are preferably morpholinyl, pyrrolidinyl, piperdinyl, piperazinyl pyridyl, pyrrolyl, imidazolyl and triazolyl, e.g. 1,2,4 triazolyl, more preferably morpholinyl, pyrollidinyl, pyridyl and imidazoyl. No heterocycle contains adjacent oxygen atoms, adjacent sulphur atoms, or adjacent oxygen and sulphur atoms.

Where a moiety is indicated as being (optionally) substituted, e.g. alkyl, this includes those moieties where they are part of a larger group, e.g. the alkyl in the alkylthio group. The same applies, e.g. to the phenyl moiety in phenylthio etc. Where a moiety is indicated as being optionally substituted by one or more other groups, preferably there are one to five optional substituents, more preferably one to three optional substituents. Where a moiety is substituted by a cyclic group, e.g. aryl, heteroaryl, cycloalkyl, preferably there are no more than two such substituents, more preferably no more than one such substituent.

The following list provides definitions, including preferred definitions, for substituents $R^1$, $R^2$, $R^3$, $R^4$, $R^5$, $R^6$, $R^7$, $R^8$, $R^9$ and $R^{10}$ with reference to compounds of formula (I). For any one of these substituents, any of the definitions given below may be combined with any definition of any other substituent given below or elsewhere in this document.

$R^1$ and $R^2$ independently represent hydrogen, $C_1$-$C_4$alkyl, $C_1$-$C_4$fluoroalkyl or $C_3$-$C_6$cycloalkyl; or $R^1$ and $R^2$ together with the nitrogen atom to which they are attached form a three to six-membered saturated cyclic group which may optionally contain one oxygen or one sulphur atom.

Preferably, $R^1$ and $R^2$ independently represent hydrogen, $C_1$-$C_4$alkyl or cyclopropyl.

More preferably, $R^1$ and $R^2$ independently represent hydrogen, methyl, ethyl, isopropyl, propyl or cyclopropyl.

Most preferably, $R^1$ represents methyl and $R^2$ represents ethyl.

$R^3$ represents fluorine, chlorine, bromine, $C_1$-$C_4$ alkyl, $C_2$-$C_4$ alkenyl, $C_1$-$C_4$ haloalkyl, $C_1$-$C_4$ alkoxy or $C_3$-$C_6$ cycloalkyl.

Preferably, $R^3$ represents fluorine, chlorine, methyl, ethyl, ethenyl, propyl, propenyl, isopropyl, isopropenyl, cyclopropanyl, methoxy, ethoxy or $C_1$-$C_2$ fluoroalkyl.

More preferably, $R^3$ represents methyl, ethyl, methoxy, fluorine or chlorine.

Even more preferably, $R^3$ represents methyl, methoxy, fluorine or chlorine.

Most preferably, $R^3$ represents methyl.

$R^4$ represents hydrogen, halogen, cyano, hydroxy, formyl, carboxy, amino, $C_1$-$C_4$ alkyl, $C_2$-$C_6$ alkenyl, $C_2$-$C_6$ alkynl, $C_1$-$C_6$ haloalkyl, $C_1$-$C_6$ alkoxy or $C_3$-$C_6$ cycloalkyl.

Preferably, $R^4$ represents hydrogen, halogen or $C_1$-$C_4$ alkyl.

More preferably, $R^4$ represents hydrogen or $C_1$-$C_4$ alkyl.

Most preferably, $R^4$ represents hydrogen.

$R^5$ represents hydrogen, halogen, cyano, $C_1$-$C_4$ alkyl, $C_1$-$C_4$ haloalkyl, $C_2$-$C_4$ alkynyl, $C_1$-$C_4$ alkoxy or $C_3$-$C_6$ cycloalkyl.

Preferably, $R^5$ represents hydrogen, halogen, cyano, $C_1$-$C_4$ alkyl, $C_1$-$C_4$ haloalkyl, cyclopropyl, ethynyl or $C_1$-$C_4$ alkoxy.

More preferably, $R^5$ represents hydrogen, bromine, iodine, chlorine, cyano, methyl, difluoromethyl, cyclopropyl, ethynyl or methoxy.

Even more preferably, $R^5$ represents hydrogen, bromine, iodine, chlorine, cyano, methyl or difluoromethyl.

Most preferably, $R^5$ represents hydrogen, bromine, cyano or methyl.

$R^6$ represents hydrogen or $C_1$-$C_4$ fluoroalkoxy.

Preferably, $R^6$ represents hydrogen or $C_1$-$C_2$ fluoroalkoxy.

More preferably, $R^6$ represents hydrogen, fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2, 2-tetrafluoroethoxy or 1,2,2,2-tetrafluoroethoxy) or pentafluoroethoxy (i.e. 1,1,2,2,2-pentafluoroethoxy).

Most preferably $R^6$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2, 2-tetrafluoroethoxy or 1,2,2,2-tetrafluoroethoxy) or pentafluoroethoxy (i.e. 1,1,2,2,2-pentafluoroethoxy).

In another group of compounds, when $R^7$ is not hydrogen, $R^6$ most preferably represents hydrogen.

$R^7$ represents hydrogen or $C_1$-$C_4$ fluoroalkoxy.

Preferably, $R^7$ represents hydrogen or $C_1$-$C_2$ fluoroalkoxy.

More preferably, $R^7$ represents hydrogen, fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

Most preferably $R^7$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

In another group of compounds, when $R^6$ is not hydrogen, $R^7$ most preferably represents hydrogen.

$R^8$ represents hydrogen or $C_1$-$C_4$ fluoroalkoxy.

Preferably, $R^8$ represents hydrogen or $C_1$-$C_2$ fluoroalkoxy.

More preferably, $R^8$ represents hydrogen, fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

Most preferably $R^8$ represents hydrogen.

$R^9$ represents hydrogen or $C_1$-$C_4$ fluoroalkoxy.

Preferably, $R^9$ represents hydrogen or $C_1$-$C_2$ fluoroalkoxy.

More preferably, $R^9$ represents hydrogen, fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

Most preferably $R^9$ represents hydrogen.

$R^{10}$ represents hydrogen or $C_1$-$C_4$ fluoroalkoxy.

Preferably, $R^{10}$ represents hydrogen or $C_1$-$C_2$ fluoroalkoxy.

More preferably, $R^{10}$ represents hydrogen, fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

Most preferably, $R^{10}$ represents hydrogen.

In one group of compounds of formula (I), $R^1$ and $R^2$ independently represent hydrogen, $C_1$-$C_4$ alkyl or cyclopropyl;

$R^3$ represents fluorine, chlorine, methyl, ethyl, ethenyl, propyl, propenyl, isopropyl, isopropenyl, cyclopropanyl, methoxy, ethoxy or $C_1$-$C_2$ fluoroalkyl;

$R^4$ represents hydrogen, halogen or $C_1$-$C_4$ alkyl;

$R^5$ represents hydrogen, halogen, cyano, $C_1$-$C_4$ alkyl, $C_1$-$C_4$ haloalkyl, cyclopropyl, ethynyl or $C_1$-$C_4$ alkoxy.

In another group of compounds of formula (I), $R^1$ and $R^2$ independently represent hydrogen, methyl, ethyl, isopropyl, propyl or cyclopropyl;

$R^3$ represents methyl, ethyl, methoxy, fluorine and chlorine;

$R^4$ represents hydrogen, halogen or $C_1$-$C_4$ alkyl;

$R^5$ represents hydrogen, bromine, iodine, chlorine, cyano, methyl, difluoromethyl, cyclopropyl, ethynyl or methoxy.

In another group of compounds of formula (I), $R^1$ and $R^2$ independently represent hydrogen, methyl, ethyl, isopropyl, propyl or cyclopropyl;

$R^3$ represents methyl, methoxy, fluorine or chlorine;

$R^4$ represents hydrogen or $C_1$-$C_4$ alkyl;

$R^5$ represents hydrogen, bromine, iodine, chlorine, cyano, methyl or difluoromethyl.

In another group of compounds of formula (I), $R^1$ represents methyl;

$R^2$ represents ethyl;

$R^3$ represents methyl, methoxy, fluorine or chlorine;

$R^4$ represents hydrogen;

$R^5$ represents hydrogen, bromine, cyano or methyl.

In another group of compounds of formula (I), $R^6$, $R^7$, $R^8$, $R^9$ and $R^{10}$ independently represent hydrogen or $C_1$-$C_4$ fluoroalkoxy;

wherein at least one of $R^6$, $R^7$, $R^8$, $R^9$ and $R^{10}$ represent $C_1$-$C_4$ fluoroalkoxy.

In another group of compounds of formula (I), $R^6$, $R^7$, $R^8$, $R^9$ and $R^{10}$ independently represent hydrogen or $C_1$-$C_2$ fluoroalkoxy;

wherein at least one of $R^6$, $R^7$, $R^8$, $R^9$ and $R^{10}$ represent $C_1$-$C_2$ fluoroalkoxy.

In another group of compounds of formula (I), $R^6$, $R^7$, $R^8$, $R^9$ and $R^{10}$ independently represent hydrogen, fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy), wherein at least one of $R^6$, $R^7$, $R^8$, $R^9$ and $R^{10}$ represent fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

In another group of compounds of formula (I), $R^9$ and $R^{10}$ are hydrogen.

In another group of compounds of formula (I), $R^8$, $R^9$ and $R^{10}$ are hydrogen.

In another group of compounds of formula (I), $R^6$, $R^8$, $R^9$ and $R^{10}$ are hydrogen.

In another group of compounds of formula (I), $R^7$, $R^8$, $R^9$ and $R^{10}$ are hydrogen.

The invention also provides a compound of formula (II)

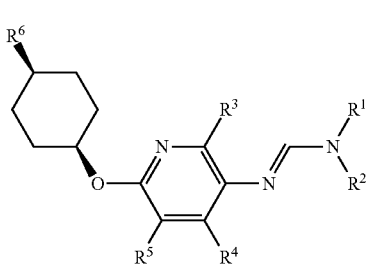
(II)

wherein $R^1$, $R^2$, $R^3$, $R^4$ and $R^5$ are as defined herein for a compound of formula (I) and $R^6$ is $C_1$-$C_4$ fluoroalkoxy. Preferred definitions of $R^1$, $R^2$, $R^3$, $R^4$ and $R^5$ given herein for a compound of formula (I) also apply to a compound of formula (II).

In the compounds of formula (II), $R^6$ preferably represents $C_1$-$C_2$ fluoroalkoxy.

Most preferably in the compounds of formula (II), $R^6$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

The invention also provides a compound of formula (III)

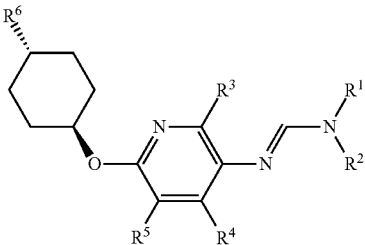
(III)

wherein $R^1$, $R^2$, $R^3$, $R^4$ and $R^5$ are as defined herein for a compound of formula (I) and $R^6$ is $C_1$-$C_4$ fluoroalkoxy. Preferred definitions of $R^1$, $R^2$, $R^3$, $R^4$ and $R^5$ given herein for a compound of formula (I) also apply to a compound of formula (III).

In the compounds of formula (III), $R^6$ preferably represents $C_1$-$C_2$ fluoroalkoxy.

Most preferably in the compounds of formula (III), $R^6$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

The invention also provides a compound of formula (IV)

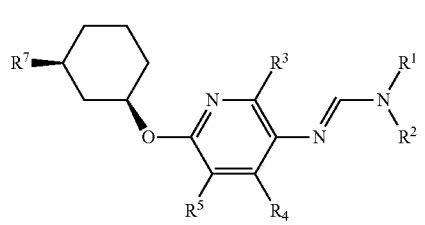
(IV)

wherein $R^1$, $R^2$, $R^3$, $R^4$ and $R^5$ are as defined herein for a compound of formula (I) and $R^7$ is $C_1$-$C_4$ fluoroalkoxy. Preferred definitions of $R^1$, $R^2$, $R^3$, $R^4$ and $R^5$ given herein for a compound of formula (I) also apply to a compound of formula (IV).

In the compounds of formula (IV), $R^7$ preferably represents $C_1$-$C_2$ fluoroalkoxy.

Most preferably in the compounds of formula (IV), $R^7$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

The invention also provides a compound of formula (V)

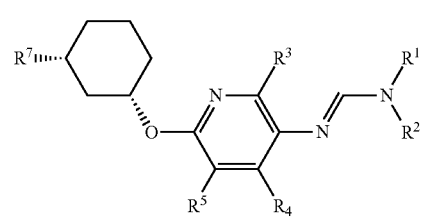
(V)

wherein $R^1$, $R^2$, $R^3$, $R^4$ and $R^5$ are as defined herein for a compound of formula (I) and $R^7$ is $C_1$-$C_4$ fluoroalkoxy. Preferred definitions of $R^1$, $R^2$, $R^3$, $R^4$ and $R^5$ given herein for a compound of formula (I) also apply to a compound of formula (V).

In the compounds of formula (V), $R^7$ preferably represents $C_1$-$C_2$ fluoroalkoxy.

Most preferably in the compounds of formula (V), $R^7$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

The invention also provides a compound of formula (VI)

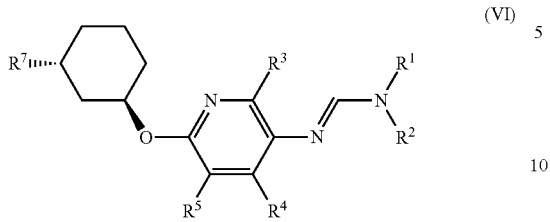

(VI)

wherein $R^1$, $R^2$, $R^3$, $R^4$ and $R^5$ are as defined herein for a compound of formula (I) and $R^7$ is $C_1$-$C_4$ fluoroalkoxy. Preferred definitions of $R^1$, $R^2$, $R^3$, $R^4$ and $R^5$ given herein for a compound of formula (I) also apply to a compound of formula (VI).

In the compounds of formula (VI), $R^7$ preferably represents $C_1$-$C_2$ fluoroalkoxy.

Most preferably in the compounds of formula (VI), $R^7$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

The invention also provides a compound of formula (VII)

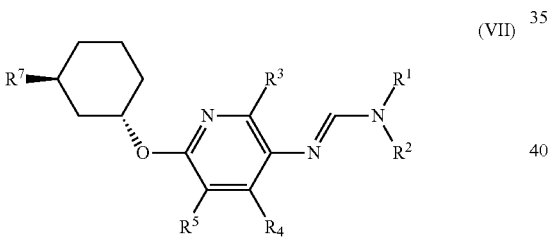

(VII)

wherein $R^1$, $R^2$, $R^3$, $R^4$ and $R^5$ are as defined herein for a compound of formula (I) and $R^7$ is $C_1$-$C_4$ fluoroalkoxy. Preferred definitions of $R^1$, $R^2$, $R^3$, $R^4$ and $R^5$ given herein for a compound of formula (I) also apply to a compound of formula (VII).

In the compounds of formula (VII), $R^7$ preferably represents $C_1$-$C_2$ fluoroalkoxy.

Most preferably in the compounds of formula (VII), $R^7$ represents fluoromethoxy, difluoromethoxy, trifluoromethoxy, fluoroethoxy (i.e. 1-fluoroethoxy or 2-fluoroethoxy), difluoroethoxy (i.e. 1,1-difluoroethoxy, 1,2-difluoroethoxy or 2,2-difluoroethoxy), trifluoroethoxy (i.e. 1,1,2-trifluoroethoxy, 1,2,2-trifluoroethoxy or 2,2,2-trifluoroethoxy), tetrafluoroethoxy (i.e. 1,1,2,2-tetrafluoroethoxy or 1,2,2,2-tetrafluoroethoxy) or pentafluoroethoxy (i.e. 1,1,2,2,2-pentafluoroethoxy).

Tables 1 to 9: Compounds of Formula (IIA)

The invention is further illustrated by making available the following individual compounds of formula (IIA) listed below in Tables 1 to 9.

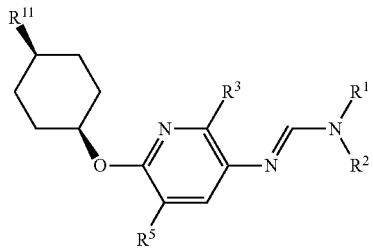

(IIA)

Each of Tables 1 to 9, which follow Table A below, make available 391 compounds of the formula (IIA) in which $R^3$, $R^5$ and $R^{11}$ are the substituents defined in Table A.

Thus Table 1 individualises 391 compounds of formula (IIA) wherein for each row of Table A, $R^1$ and $R^2$ are as defined in Table 1. Similarly, Table 2 individualises 391 compounds of formula (IIA) wherein for each row of Table A, $R^1$ and $R^2$ are is as defined in Table 2; and so on for Tables 3 to 9.

Table A discloses 391 sets of meanings of the variables $R^3$, $R^5$ and $R^{11}$ in a compound of formula (IIA).

Tables 10 to 18: Compounds of Formula (IIIA)

The invention is further illustrated by making available the following individual compounds of formula (IIIA) listed below in Tables 10 to 18.

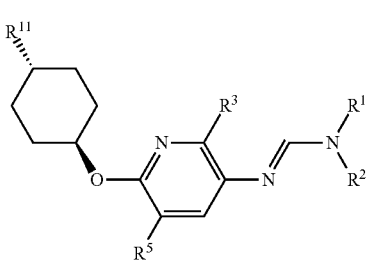

(IIIA)

Each of Tables 10 to 18, which follow Table A below, make available 391 compounds of the formula (IIIA) in which $R^3$, $R^5$ and $R^{11}$ are the substituents defined in Table A.

Thus Table 10 individualises 391 compounds of formula (IIIA) wherein for each row of Table A, $R^1$ and $R^2$ are as defined in Table 10. Similarly, Table 11 individualises 391 compounds of formula (IIIA) wherein for each row of Table A, $R^1$ and $R^2$ are is as defined in Table 11; and so on for Tables 12 to 18.

Table A discloses 391 sets of meanings of the variables $R^3$, $R^5$ and $R^{11}$ in a compound of formula (IIIA).

Tables 19 to 27: Compounds of Formula (IVA)

The invention is further illustrated by making available the following individual compounds of formula (IVA) listed below in Tables 19 to 27.

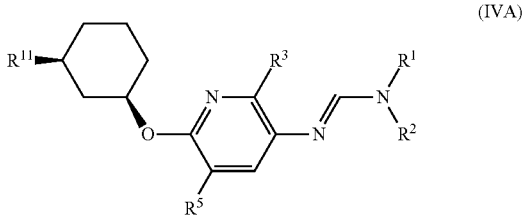

(IVA)

Each of Tables 19 to 27, which follow Table A below, make available 391 compounds of the formula (IVA) in which $R^3$, $R^5$ and $R^{11}$ are the substituents defined in Table A.

Thus Table 19 individualises 391 compounds of formula (IVA) wherein for each row of Table A, $R^1$ and $R^2$ are as defined in Table 19. Similarly, Table 20 individualises 391 compounds of formula (IVA) wherein for each row of Table A, $R^1$ and $R^2$ are is as defined in Table 20; and so on for Tables 21 to 27.

Table A discloses 391 sets of meanings of the variables $R^3$, $R^5$ and $R^{11}$ in a compound of formula (IVA).

Tables 28 to 36: Compounds of Formula (VA)

The invention is further illustrated by making available the following individual compounds of formula (VA) listed below in Tables 28 to 36.

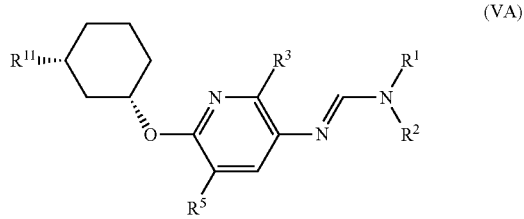

(VA)

Each of Tables 28 to 36, which follow Table A below, make available 391 compounds of the formula (IVA) in which $R^3$, $R^5$ and $R^{11}$ are the substituents defined in Table A.

Thus Table 28 individualises 391 compounds of formula (VA) wherein for each row of Table A, $R^1$ and $R^2$ are as defined in Table 28. Similarly, Table 29 individualises 391 compounds of formula (VA) wherein for each row of Table A, $R^1$ and $R^2$ are is as defined in Table 29; and so on for Tables 30 to 36.

Table A discloses 391 sets of meanings of the variables $R^3$, $R^5$ and $R^{11}$ in a compound of formula (VA).

Tables 37 to 45: Compounds of Formula (VIA)

The invention is further illustrated by making available the following individual compounds of formula (VIA) listed below in Tables 37 to 45.

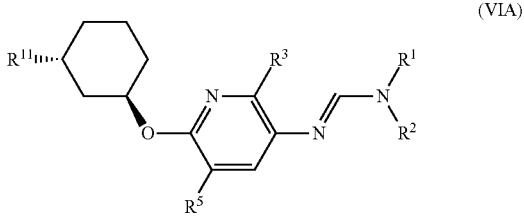

(VIA)

Each of Tables 37 to 45, which follow Table A below, make available 391 compounds of the formula (VIA) in which $R^3$, $R^5$ and $R^{11}$ are the substituents defined in Table A.

Thus Table 28 individualises 391 compounds of formula (VIA) wherein for each row of Table A, $R^1$ and $R^2$ are as defined in Table 37. Similarly, Table 38 individualises 391 compounds of formula (VIA) wherein for each row of Table A, $R^1$ and $R^2$ are is as defined in Table 38; and so on for Tables 39 to 45.

Table A discloses 391 sets of meanings of the variables $R^3$, $R^5$ and $R^{11}$ in a compound of formula (VIA).

Tables 46 to 54: Compounds of Formula (VIIA)

The invention is further illustrated by making available the following individual compounds of formula (VIIA) listed below in Tables 46 to 54.

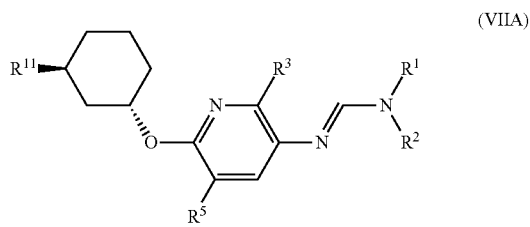

(VIIA)

Each of Tables to 54, which follow Table A below, male available 391 compounds of the formula (VIIA) in which $R^3$, $R^5$ and $R^{11}$ are the substituents defined in Table A.

Thus Table 46 individualises 391 compounds of formula (VIIA) wherein for each row of Table A, $R^1$ and $R^2$ are as defined in Table 46. Similarly, Table 47 individualises 391 compounds of formula (VIIA) wherein for each row of Table A, $R^1$ and $R^2$ are is as defined in Table 47; and so on for Tables 48 to 54.

Table A discloses 391 sets of meanings of the variables $R^3$, $R^5$ and $R^{11}$ in a compound of formula (VIIA).

TABLE A

|  | R3 | R5 | R11 |
|---|---|---|---|
| A.1 | hydrogen | hydrogen | fluoromethoxy |
| A.2 | methyl | hydrogen | fluoromethoxy |
| A.3 | ethyl | hydrogen | fluoromethoxy |
| A.4 | isopropyl | hydrogen | fluoromethoxy |
| A.5 | cyclopropyl | hydrogen | fluoromethoxy |
| A.6 | chlorine | hydrogen | fluoromethoxy |
| A.7 | hydrogen | chlorine | fluoromethoxy |
| A.8 | methyl | chlorine | fluoromethoxy |
| A.9 | ethyl | chlorine | fluoromethoxy |
| A.10 | isopropyl | chlorine | fluoromethoxy |
| A.11 | cyclopropyl | chlorine | fluoromethoxy |
| A.12 | chlorine | chlorine | fluoromethoxy |
| A.13 | hydrogen | bromine | fluoromethoxy |
| A.14 | methyl | bromine | fluoromethoxy |
| A.15 | ethyl | bromine | fluoromethoxy |
| A.16 | isopropyl | bromine | fluoromethoxy |
| A.17 | cyclopropyl | bromine | fluoromethoxy |
| A.18 | chlorine | bromine | fluoromethoxy |
| A.19 | hydrogen | iodine | fluoromethoxy |
| A.20 | methyl | iodine | fluoromethoxy |
| A.21 | ethyl | iodine | fluoromethoxy |
| A.22 | isopropyl | iodine | fluoromethoxy |
| A.23 | cyclopropyl | iodine | fluoromethoxy |
| A.24 | chlorine | iodine | fluoromethoxy |
| A.25 | hydrogen | cyano | fluoromethoxy |
| A.26 | methyl | cyano | fluoromethoxy |
| A.27 | ethyl | cyano | fluoromethoxy |
| A.28 | isopropyl | cyano | fluoromethoxy |
| A.29 | cyclopropyl | cyano | fluoromethoxy |
| A.30 | chlorine | cyano | fluoromethoxy |
| A.31 | hydrogen | methyl | fluoromethoxy |
| A.32 | methyl | methyl | fluoromethoxy |
| A.33 | ethyl | methyl | fluoromethoxy |

TABLE A-continued

| | R3 | R5 | R11 |
|---|---|---|---|
| A.34 | isopropyl | methyl | fluoromethoxy |
| A.35 | cyclopropyl | methyl | fluoromethoxy |
| A.36 | chlorine | methyl | fluoromethoxy |
| A.37 | hydrogen | ethyl | fluoromethoxy |
| A.38 | methyl | ethyl | fluoromethoxy |
| A.39 | ethyl | ethyl | fluoromethoxy |
| A.40 | isopropyl | ethyl | fluoromethoxy |
| A.41 | cyclopropyl | ethyl | fluoromethoxy |
| A.42 | chlorine | ethyl | fluoromethoxy |
| A.43 | hydrogen | cyclopropyl | fluoromethoxy |
| A.44 | methyl | cyclopropyl | fluoromethoxy |
| A.45 | ethyl | cyclopropyl | fluoromethoxy |
| A.46 | isopropyl | cyclopropyl | fluoromethoxy |
| A.47 | cyclopropyl | cyclopropyl | fluoromethoxy |
| A.48 | chlorine | cyclopropyl | fluoromethoxy |
| A.49 | hydrogen | difluoromethyl | fluoromethoxy |
| A.50 | methyl | difluoromethyl | fluoromethoxy |
| A.51 | ethyl | difluoromethyl | fluoromethoxy |
| A.52 | isopropyl | difluoromethyl | fluoromethoxy |
| A.53 | cyclopropyl | difluoromethyl | fluoromethoxy |
| A.54 | chlorine | difluoromethyl | fluoromethoxy |
| A.55 | hydrogen | trifluoromethyl | fluoromethoxy |
| A.56 | methyl | trifluoromethyl | fluoromethoxy |
| A.57 | ethyl | trifluoromethyl | fluoromethoxy |
| A.58 | isopropyl | trifluoromethyl | fluoromethoxy |
| A.59 | cyclopropyl | trifluoromethyl | fluoromethoxy |
| A.60 | chlorine | trifluoromethyl | fluoromethoxy |
| A.61 | hydrogen | ethynyl | fluoromethoxy |
| A.62 | methyl | ethynyl | fluoromethoxy |
| A.63 | ethyl | ethynyl | fluoromethoxy |
| A.64 | isopropyl | ethynyl | fluoromethoxy |
| A.65 | cyclopropyl | ethynyl | fluoromethoxy |
| A.66 | chlorine | ethynyl | fluoromethoxy |
| A.67 | hydrogen | methoxy | fluoromethoxy |
| A.68 | methyl | methoxy | fluoromethoxy |
| A.69 | ethyl | methoxy | fluoromethoxy |
| A.70 | isopropyl | methoxy | fluoromethoxy |
| A.71 | cyclopropyl | methoxy | fluoromethoxy |
| A.72 | chlorine | methoxy | fluoromethoxy |
| A.73 | hydrogen | difluoromethoxy | fluoromethoxy |
| A.74 | methyl | difluoromethoxy | fluoromethoxy |
| A.75 | ethyl | difluoromethoxy | fluoromethoxy |
| A.76 | isopropyl | difluoromethoxy | fluoromethoxy |
| A.77 | cyclopropyl | difluoromethoxy | fluoromethoxy |
| A.78 | chlorine | difluoromethoxy | fluoromethoxy |
| A.79 | hydrogen | hydrogen | difluoromethoxy |
| A.80 | methyl | hydrogen | difluoromethoxy |
| A.81 | ethyl | hydrogen | difluoromethoxy |
| A.82 | isopropyl | hydrogen | difluoromethoxy |
| A.83 | cyclopropyl | hydrogen | difluoromethoxy |
| A.84 | chlorine | hydrogen | difluoromethoxy |
| A.85 | hydrogen | chlorine | difluoromethoxy |
| A.86 | methyl | chlorine | difluoromethoxy |
| A.87 | ethyl | chlorine | difluoromethoxy |
| A.88 | isopropyl | chlorine | difluoromethoxy |
| A.89 | cyclopropyl | chlorine | difluoromethoxy |
| A.90 | chlorine | chlorine | difluoromethoxy |
| A.91 | hydrogen | bromine | difluoromethoxy |
| A.92 | methyl | bromine | difluoromethoxy |
| A.93 | ethyl | bromine | difluoromethoxy |
| A.94 | isopropyl | bromine | difluoromethoxy |
| A.95 | cyclopropyl | bromine | difluoromethoxy |
| A.96 | chlorine | bromine | difluoromethoxy |
| A.97 | hydrogen | iodine | difluoromethoxy |
| A.98 | methyl | iodine | difluoromethoxy |
| A.99 | ethyl | iodine | difluoromethoxy |
| A.100 | isopropyl | iodine | difluoromethoxy |
| A.101 | cyclopropyl | iodine | difluoromethoxy |
| A.102 | chlorine | iodine | difluoromethoxy |
| A.103 | hydrogen | cyano | difluoromethoxy |
| A.104 | methyl | cyano | difluoromethoxy |
| A.105 | ethyl | cyano | difluoromethoxy |
| A.106 | isopropyl | cyano | difluoromethoxy |
| A.107 | cyclopropyl | cyano | difluoromethoxy |
| A.108 | chlorine | cyano | difluoromethoxy |
| A.109 | hydrogen | methyl | difluoromethoxy |
| A.110 | methyl | methyl | difluoromethoxy |
| A.111 | ethyl | methyl | difluoromethoxy |
| A.112 | isopropyl | methyl | difluoromethoxy |
| A.113 | cyclopropyl | methyl | difluoromethoxy |
| A.114 | chlorine | methyl | difluoromethoxy |
| A.115 | hydrogen | ethyl | difluoromethoxy |
| A.116 | methyl | ethyl | difluoromethoxy |
| A.117 | ethyl | ethyl | difluoromethoxy |
| A.118 | isopropyl | ethyl | difluoromethoxy |
| A.119 | cyclopropyl | ethyl | difluoromethoxy |
| A.120 | chlorine | ethyl | difluoromethoxy |
| A.121 | hydrogen | cyclopropyl | difluoromethoxy |
| A.122 | methyl | cyclopropyl | difluoromethoxy |
| A.123 | ethyl | cyclopropyl | difluoromethoxy |
| A.124 | isopropyl | cyclopropyl | difluoromethoxy |
| A.125 | cyclopropyl | cyclopropyl | difluoromethoxy |
| A.126 | chlorine | cyclopropyl | difluoromethoxy |
| A.127 | hydrogen | difluoromethyl | difluoromethoxy |
| A.128 | methyl | difluoromethyl | difluoromethoxy |
| A.129 | ethyl | difluoromethyl | difluoromethoxy |
| A.130 | isopropyl | difluoromethyl | difluoromethoxy |
| A.131 | cyclopropyl | difluoromethyl | difluoromethoxy |
| A.132 | chlorine | difluoromethyl | difluoromethoxy |
| A.133 | hydrogen | trifluoromethyl | difluoromethoxy |
| A.134 | methyl | trifluoromethyl | difluoromethoxy |
| A.135 | ethyl | trifluoromethyl | difluoromethoxy |
| A.136 | isopropyl | trifluoromethyl | difluoromethoxy |
| A.137 | cyclopropyl | trifluoromethyl | difluoromethoxy |
| A.138 | chlorine | trifluoromethyl | difluoromethoxy |
| A.139 | hydrogen | ethynyl | difluoromethoxy |
| A.140 | methyl | ethynyl | difluoromethoxy |
| A.141 | ethyl | ethynyl | difluoromethoxy |
| A.142 | isopropyl | ethynyl | difluoromethoxy |
| A.143 | cyclopropyl | ethynyl | difluoromethoxy |
| A.144 | chlorine | ethynyl | difluoromethoxy |
| A.145 | hydrogen | methoxy | difluoromethoxy |
| A.146 | methyl | methoxy | difluoromethoxy |
| A.147 | ethyl | methoxy | difluoromethoxy |
| A.148 | isopropyl | methoxy | difluoromethoxy |
| A.149 | cyclopropyl | methoxy | difluoromethoxy |
| A.150 | chlorine | methoxy | difluoromethoxy |
| A.151 | hydrogen | difluoromethoxy | difluoromethoxy |
| A.152 | methyl | difluoromethoxy | difluoromethoxy |
| A.153 | ethyl | difluoromethoxy | difluoromethoxy |
| A.154 | isopropyl | difluoromethoxy | difluoromethoxy |
| A.155 | cyclopropyl | difluoromethoxy | difluoromethoxy |
| A.156 | chlorine | difluoromethoxy | difluoromethoxy |
| A.157 | hydrogen | hydrogen | trifluoromethoxy |
| A.158 | methyl | hydrogen | trifluoromethoxy |
| A.159 | ethyl | hydrogen | trifluoromethoxy |
| A.160 | isopropyl | hydrogen | trifluoromethoxy |
| A.161 | cyclopropyl | hydrogen | trifluoromethoxy |
| A.162 | chlorine | hydrogen | trifluoromethoxy |
| A.163 | hydrogen | chlorine | trifluoromethoxy |
| A.164 | methyl | chlorine | trifluoromethoxy |
| A.165 | ethyl | chlorine | trifluoromethoxy |
| A.166 | isopropyl | chlorine | trifluoromethoxy |
| A.167 | cyclopropyl | chlorine | trifluoromethoxy |
| A.168 | chlorine | chlorine | trifluoromethoxy |
| A.169 | hydrogen | bromine | trifluoromethoxy |
| A.170 | methyl | bromine | trifluoromethoxy |
| A.171 | ethyl | bromine | trifluoromethoxy |
| A.172 | isopropyl | bromine | trifluoromethoxy |
| A.173 | cyclopropyl | bromine | trifluoromethoxy |
| A.174 | chlorine | bromine | trifluoromethoxy |
| A.175 | hydrogen | iodine | trifluoromethoxy |
| A.176 | methyl | iodine | trifluoromethoxy |
| A.177 | ethyl | iodine | trifluoromethoxy |
| A.178 | isopropyl | iodine | trifluoromethoxy |
| A.179 | cyclopropyl | iodine | trifluoromethoxy |
| A.180 | chlorine | iodine | trifluoromethoxy |
| A.181 | hydrogen | cyano | trifluoromethoxy |
| A.182 | methyl | cyano | trifluoromethoxy |
| A.183 | ethyl | cyano | trifluoromethoxy |
| A.184 | isopropyl | cyano | trifluoromethoxy |
| A.185 | cyclopropyl | cyano | trifluoromethoxy |
| A.186 | chlorine | cyano | trifluoromethoxy |
| A.187 | hydrogen | methyl | trifluoromethoxy |
| A.188 | methyl | methyl | trifluoromethoxy |
| A.189 | ethyl | methyl | trifluoromethoxy |

TABLE A-continued

| | R3 | R5 | R11 |
|---|---|---|---|
| A.190 | isopropyl | methyl | trifluoromethoxy |
| A.191 | cyclopropyl | methyl | trifluoromethoxy |
| A.192 | chlorine | methyl | trifluoromethoxy |
| A.193 | hydrogen | ethyl | trifluoromethoxy |
| A.194 | methyl | ethyl | trifluoromethoxy |
| A.195 | ethyl | ethyl | trifluoromethoxy |
| A.196 | isopropyl | ethyl | trifluoromethoxy |
| A.197 | cyclopropyl | ethyl | trifluoromethoxy |
| A.198 | chlorine | ethyl | trifluoromethoxy |
| A.199 | hydrogen | cyclopropyl | trifluoromethoxy |
| A.200 | methyl | cyclopropyl | trifluoromethoxy |
| A.201 | ethyl | cyclopropyl | trifluoromethoxy |
| A.202 | isopropyl | cyclopropyl | trifluoromethoxy |
| A.203 | cyclopropyl | cyclopropyl | trifluoromethoxy |
| A.204 | chlorine | cyclopropyl | trifluoromethoxy |
| A.205 | hydrogen | difluoromethyl | trifluoromethoxy |
| A.206 | methyl | difluoromethyl | trifluoromethoxy |
| A.207 | ethyl | difluoromethyl | trifluoromethoxy |
| A.208 | isopropyl | difluoromethyl | trifluoromethoxy |
| A.209 | cyclopropyl | difluoromethyl | trifluoromethoxy |
| A.210 | chlorine | difluoromethyl | trifluoromethoxy |
| A.211 | hydrogen | trifluoromethyl | trifluoromethoxy |
| A.212 | methyl | trifluoromethyl | trifluoromethoxy |
| A.213 | ethyl | trifluoromethyl | trifluoromethoxy |
| A.214 | isopropyl | trifluoromethyl | trifluoromethoxy |
| A.215 | cyclopropyl | trifluoromethyl | trifluoromethoxy |
| A.216 | chlorine | trifluoromethyl | trifluoromethoxy |
| A.217 | hydrogen | ethynyl | trifluoromethoxy |
| A.218 | methyl | ethynyl | trifluoromethoxy |
| A.219 | ethyl | ethynyl | trifluoromethoxy |
| A.220 | isopropyl | ethynyl | trifluoromethoxy |
| A.221 | cyclopropyl | ethynyl | trifluoromethoxy |
| A.222 | chlorine | ethynyl | trifluoromethoxy |
| A.223 | hydrogen | methoxy | trifluoromethoxy |
| A.224 | methyl | methoxy | trifluoromethoxy |
| A.225 | ethyl | methoxy | trifluoromethoxy |
| A.226 | isopropyl | methoxy | trifluoromethoxy |
| A.227 | cyclopropyl | methoxy | trifluoromethoxy |
| A.228 | chlorine | methoxy | trifluoromethoxy |
| A.229 | hydrogen | difluoromethoxy | trifluoromethoxy |
| A.230 | methyl | difluoromethoxy | trifluoromethoxy |
| A.231 | ethyl | difluoromethoxy | trifluoromethoxy |
| A.232 | isopropyl | difluoromethoxy | trifluoromethoxy |
| A.233 | cyclopropyl | difluoromethoxy | trifluoromethoxy |
| A.234 | chlorine | difluoromethoxy | trifluoromethoxy |
| A.235 | hydrogen | hydrogen | 1,1-difluoroethoxy |
| A.236 | methyl | hydrogen | 1,1-difluoroethoxy |
| A.237 | ethyl | hydrogen | 1,1-difluoroethoxy |
| A.238 | isopropyl | hydrogen | 1,1-difluoroethoxy |
| A.239 | cyclopropyl | hydrogen | 1,1-difluoroethoxy |
| A.240 | chlorine | hydrogen | 1,1-difluoroethoxy |
| A.241 | hydrogen | chlorine | 1,1-difluoroethoxy |
| A.242 | methyl | chlorine | 1,1-difluoroethoxy |
| A.243 | ethyl | chlorine | 1,1-difluoroethoxy |
| A.244 | isopropyl | chlorine | 1,1-difluoroethoxy |
| A.245 | cyclopropyl | chlorine | 1,1-difluoroethoxy |
| A.246 | chlorine | chlorine | 1,1-difluoroethoxy |
| A.247 | hydrogen | bromine | 1,1-difluoroethoxy |
| A.248 | methyl | bromine | 1,1-difluoroethoxy |
| A.249 | ethyl | bromine | 1,1-difluoroethoxy |
| A.250 | isopropyl | bromine | 1,1-difluoroethoxy |
| A.251 | cyclopropyl | bromine | 1,1-difluoroethoxy |
| A.252 | chlorine | bromine | 1,1-difluoroethoxy |
| A.253 | hydrogen | iodine | 1,1-difluoroethoxy |
| A.254 | methyl | iodine | 1,1-difluoroethoxy |
| A.255 | ethyl | iodine | 1,1-difluoroethoxy |
| A.256 | isopropyl | iodine | 1,1-difluoroethoxy |
| A.257 | cyclopropyl | iodine | 1,1-difluoroethoxy |
| A.258 | chlorine | iodine | 1,1-difluoroethoxy |
| A.259 | hydrogen | cyano | 1,1-difluoroethoxy |
| A.260 | methyl | cyano | 1,1-difluoroethoxy |
| A.261 | ethyl | cyano | 1,1-difluoroethoxy |
| A.262 | isopropyl | cyano | 1,1-difluoroethoxy |
| A.263 | cyclopropyl | cyano | 1,1-difluoroethoxy |
| A.264 | chlorine | cyano | 1,1-difluoroethoxy |
| A.265 | hydrogen | methyl | 1,1-difluoroethoxy |
| A.266 | methyl | methyl | 1,1-difluoroethoxy |
| A.267 | ethyl | methyl | 1,1-difluoroethoxy |
| A.268 | isopropyl | methyl | 1,1-difluoroethoxy |
| A.269 | cyclopropyl | methyl | 1,1-difluoroethoxy |
| A.270 | chlorine | methyl | 1,1-difluoroethoxy |
| A.271 | hydrogen | ethyl | 1,1-difluoroethoxy |
| A.272 | methyl | ethyl | 1,1-difluoroethoxy |
| A.273 | ethyl | ethyl | 1,1-difluoroethoxy |
| A.274 | isopropyl | ethyl | 1,1-difluoroethoxy |
| A.275 | cyclopropyl | ethyl | 1,1-difluoroethoxy |
| A.276 | chlorine | ethyl | 1,1-difluoroethoxy |
| A.277 | hydrogen | cyclopropyl | 1,1-difluoroethoxy |
| A.278 | methyl | cyclopropyl | 1,1-difluoroethoxy |
| A.279 | ethyl | cyclopropyl | 1,1-difluoroethoxy |
| A.280 | isopropyl | cyclopropyl | 1,1-difluoroethoxy |
| A.281 | cyclopropyl | cyclopropyl | 1,1-difluoroethoxy |
| A.282 | chlorine | cyclopropyl | 1,1-difluoroethoxy |
| A.283 | hydrogen | difluoromethyl | 1,1-difluoroethoxy |
| A.284 | methyl | difluoromethyl | 1,1-difluoroethoxy |
| A.285 | ethyl | difluoromethyl | 1,1-difluoroethoxy |
| A.286 | isopropyl | difluoromethyl | 1,1-difluoroethoxy |
| A.287 | cyclopropyl | difluoromethyl | 1,1-difluoroethoxy |
| A.288 | chlorine | difluoromethyl | 1,1-difluoroethoxy |
| A.289 | hydrogen | trifluoromethyl | 1,1-difluoroethoxy |
| A.290 | methyl | trifluoromethyl | 1,1-difluoroethoxy |
| A.291 | ethyl | trifluoromethyl | 1,1-difluoroethoxy |
| A.292 | isopropyl | trifluoromethyl | 1,1-difluoroethoxy |
| A.293 | cyclopropyl | trifluoromethyl | 1,1-difluoroethoxy |
| A.294 | chlorine | trifluoromethyl | 1,1-difluoroethoxy |
| A.295 | hydrogen | ethynyl | 1,1-difluoroethoxy |
| A.296 | methyl | ethynyl | 1,1-difluoroethoxy |
| A.297 | ethyl | ethynyl | 1,1-difluoroethoxy |
| A.298 | isopropyl | ethynyl | 1,1-difluoroethoxy |
| A.299 | cyclopropyl | ethynyl | 1,1-difluoroethoxy |
| A.300 | chlorine | ethynyl | 1,1-difluoroethoxy |
| A.301 | hydrogen | methoxy | 1,1-difluoroethoxy |
| A.302 | methyl | methoxy | 1,1-difluoroethoxy |
| A.303 | ethyl | methoxy | 1,1-difluoroethoxy |
| A.304 | isopropyl | methoxy | 1,1-difluoroethoxy |
| A.305 | cyclopropyl | methoxy | 1,1-difluoroethoxy |
| A.306 | chlorine | methoxy | 1,1-difluoroethoxy |
| A.307 | hydrogen | difluoromethoxy | 1,1-difluoroethoxy |
| A.308 | methyl | difluoromethoxy | 1,1-difluoroethoxy |
| A.309 | ethyl | difluoromethoxy | 1,1-difluoroethoxy |
| A.310 | isopropyl | difluoromethoxy | 1,1-difluoroethoxy |
| A.311 | cyclopropyl | difluoromethoxy | 1,1-difluoroethoxy |
| A.312 | chlorine | difluoromethoxy | 1,1-difluoroethoxy |
| A.313 | methyl | hydrogen | 1-fluoroethoxy |
| A.314 | methyl | bromine | 1-fluoroethoxy |
| A.315 | methyl | iodine | 1-fluoroethoxy |
| A.316 | methyl | methyl | 1-fluoroethoxy |
| A.317 | methyl | cyclopropyl | 1-fluoroethoxy |
| A.318 | methyl | ethynyl | 1-fluoroethoxy |
| A.319 | methyl | methoxy | 1-fluoroethoxy |
| A.320 | methyl | hydrogen | 2-fluoroethoxy |
| A.321 | methyl | bromine | 2-fluoroethoxy |
| A.322 | methyl | iodine | 2-fluoroethoxy |
| A.323 | methyl | methyl | 2-fluoroethoxy |
| A.324 | methyl | cyclopropyl | 2-fluoroethoxy |
| A.325 | methyl | ethynyl | 2-fluoroethoxy |
| A.326 | methyl | methoxy | 2-fluoroethoxy |
| A.327 | methyl | hydrogen | 1,2-difluoroethoxy |
| A.328 | methyl | bromine | 1,2-difluoroethoxy |
| A.329 | methyl | iodine | 1,2-difluoroethoxy |
| A.330 | methyl | methyl | 1,2-difluoroethoxy |
| A.331 | methyl | cyclopropyl | 1,2-difluoroethoxy |
| A.332 | methyl | ethynyl | 1,2-difluoroethoxy |
| A.333 | methyl | methoxy | 1,2-difluoroethoxy |
| A.334 | methyl | hydrogen | 2,2-difluoroethoxy |
| A.335 | methyl | bromine | 2,2-difluoroethoxy |
| A.336 | methyl | iodine | 2,2-difluoroethoxy |
| A.337 | methyl | methyl | 2,2-difluoroethoxy |
| A.338 | methyl | cyclopropyl | 2,2-difluoroethoxy |
| A.339 | methyl | ethynyl | 2,2-difluoroethoxy |
| A.340 | methyl | methoxy | 2,2-difluoroethoxy |
| A.341 | methyl | hydrogen | 1,1,2-trifluoroethoxy |
| A.342 | methyl | bromine | 1,1,2-trifluoroethoxy |
| A.343 | methyl | iodine | 1,1,2-trifluoroethoxy |
| A.344 | methyl | methyl | 1,1,2-trifluoroethoxy |
| A.345 | methyl | cyclopropyl | 1,1,2-trifluoroethoxy |

TABLE A-continued

| | R3 | R5 | R11 |
|---|---|---|---|
| A.346 | methyl | ethynyl | 1,1,2-trifluoroethoxy |
| A.347 | methyl | methoxy | 1,1,2-trifluoroethoxy |
| A.348 | methyl | hydrogen | 1,2,2-trifluoroethoxy |
| A.349 | methyl | bromine | 1,2,2-trifluoroethoxy |
| A.350 | methyl | iodine | 1,2,2-trifluoroethoxy |
| A.351 | methyl | methyl | 1,2,2-trifluoroethoxy |
| A.352 | methyl | cyclopropyl | 1,2,2-trifluoroethoxy |
| A.353 | methyl | ethynyl | 1,2,2-trifluoroethoxy |
| A.354 | methyl | methoxy | 1,2,2-trifluoroethoxy |
| A.355 | methyl | hydrogen | 2,2,2-trifluoroethoxy |
| A.356 | methyl | bromine | 2,2,2-trifluoroethoxy |
| A.357 | methyl | iodine | 2,2,2-trifluoroethoxy |
| A.358 | methyl | methyl | 2,2,2-trifluoroethoxy |
| A.359 | methyl | cyclopropyl | 2,2,2-trifluoroethoxy |
| A.360 | methyl | ethynyl | 2,2,2-trifluoroethoxy |
| A.361 | methyl | methoxy | 2,2,2-trifluoroethoxy |
| A.362 | methyl | hydrogen | 1,1,2,2-tetrafluoroethoxy |
| A.363 | methyl | bromine | 1,1,2,2-tetrafluoroethoxy |
| A.364 | methyl | iodine | 1,1,2,2-tetrafluoroethoxy |
| A.365 | methyl | methyl | 1,1,2,2-tetrafluoroethoxy |
| A.366 | methyl | cyclopropyl | 1,1,2,2-tetrafluoroethoxy |
| A.367 | methyl | ethynyl | 1,1,2,2-tetrafluoroethoxy |
| A.368 | methyl | methoxy | 1,1,2,2-tetrafluoroethoxy |
| A.369 | methyl | hydrogen | 1,2,2,2-tetrafluoroethoxy |
| A.370 | methyl | bromine | 1,2,2,2-tetrafluoroethoxy |
| A.371 | methyl | iodine | 1,2,2,2-tetrafluoroethoxy |
| A.372 | methyl | methyl | 1,2,2,2-tetrafluoroethoxy |
| A.373 | methyl | cyclopropyl | 1,2,2,2-tetrafluoroethoxy |
| A.374 | methyl | ethynyl | 1,2,2,2-tetrafluoroethoxy |
| A.375 | methyl | methoxy | 1,2,2,2-tetrafluoroethoxy |
| A.376 | methyl | hydrogen | 1,1,2,2,2-pentafluoroethoxy |
| A.377 | methyl | bromine | 1,1,2,2,2-pentafluoroethoxy |
| A.378 | methyl | iodine | 1,1,2,2,2-pentafluoroethoxy |
| A.379 | methyl | methyl | 1,1,2,2,2-pentafluoroethoxy |
| A.380 | methyl | cyclopropyl | 1,1,2,2,2-pentafluoroethoxy |
| A.381 | methyl | ethynyl | 1,1,2,2,2-pentafluoroethoxy |
| A.382 | methyl | methoxy | 1,1,2,2,2-pentafluoroethoxy |
| A.383 | methyl | iodine | 1,2-difluoroethoxy |
| A.384 | methyl | methyl | 1,2-difluoroethoxy |
| A.385 | methyl | cyclopropyl | 1,2-difluoroethoxy |
| A.386 | methyl | ethynyl | 1,2-difluoroethoxy |
| A.387 | methyl | methoxy | 1,2-difluoroethoxy |
| A.388 | methyl | hydrogen | 2,2-difluoroethoxy |
| A.389 | methyl | bromine | 2,2-difluoroethoxy |
| A.390 | methyl | iodine | 2,2-difluoroethoxy |
| A.391 | methyl | methyl | 2,2-difluoroethoxy |

Table 1:

Table 1 discloses 391 compounds of formula (IIA) wherein $R^1$ is methyl, $R^2$ is ethyl and each of the variables $R^3$, $R^5$ and $R^{11}$ has the specific meaning given in the corresponding row of Table A. For example, compound 1.1 has the following structure:

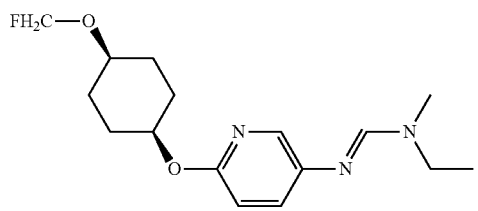

Table 2:

Table 2 discloses 391 compounds of formula (IIA) wherein $R^1$ is ethyl, $R^2$ is ethyl and each of the variables $R^3$, $R^5$ and $R^{11}$ has the specific meaning given in the corresponding row of Table A.

Table 3:

Table 3 discloses 391 compounds of formula (IIA) wherein $R^1$ is methyl, $R^2$ is cyclopropyl and each of the variables $R^3$, $R^5$ and $R^{11}$ has the specific meaning given in the corresponding row of Table A.

Table 4:

Table 4 discloses 391 compounds of formula (IIA) wherein $R^1$ is methyl, $R^2$ is isopropyl and each of the variables $R^3$, $R^5$ and $R^{11}$ has the specific meaning given in the corresponding row of Table A.

Table 5:

Table 5 discloses 391 compounds of formula (IIA) wherein $R^1$ is methyl, $R^2$ is methyl and each of the variables $R^3$, $R^5$ and $R^{11}$ has the specific meaning given in the corresponding row of Table A.

Table 6:

Table 6 discloses 391 compounds of formula (IIA) wherein $R^1$ is ethyl, $R^2$ is hydrogen and each of the variables $R^3$, $R^5$ and $R^{11}$ has the specific meaning given in the corresponding row of Table A.

Table 7:

Table 7 discloses 391 compounds of formula (IIA) wherein $R^1$ is methyl, $R^2$ is hydrogen and each of the variables $R^3$, $R^5$ and $R^{11}$ has the specific meaning given in the corresponding row of Table A.

Table 8:

Table 8 discloses 391 compounds of formula (IIA) wherein $R^1$ is isopropyl, $R^2$ is hydrogen and each of the variables $R^3$, $R^5$ and $R^{11}$ has the specific meaning given in the corresponding row of Table A.

Table 9:

Table 9 discloses 391 compounds of formula (IIA) wherein $R^1$ and $R^2$ together form a four-membered alkylene bridge and each of the variables $R^3$, $R^5$ and $R^{11}$ has the specific meaning given in the corresponding row of Table A. For example, compound 9.1 has the following structure:

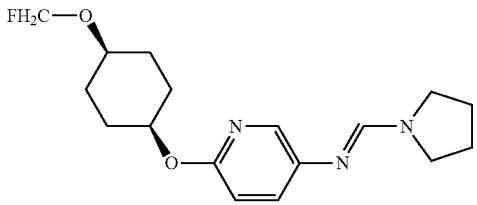

Table 10:

Table 10 discloses 391 compounds of formula (IIIA) wherein $R^1$ is methyl, $R^2$ is ethyl and each of the variables $R^3$, $R^5$ and $R^{11}$ has the specific meaning given in the corresponding row of Table A. For example, compound 10.1 has the following structure:

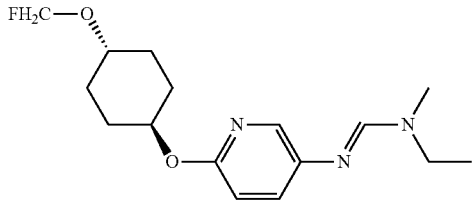

Table 11:

Table 11 discloses 391 compounds of formula (IIIA) wherein $R^1$ is ethyl, $R^2$ is ethyl and each of the variables $R^3$, $R^5$ and $R^{11}$ has the specific meaning given in the corresponding row of Table A.

Table 12:
Table 12 discloses 391 compounds of formula (IIIA) wherein $R^1$ is methyl, $R^2$ is cyclopropyl and each of the variables $R^3$, $R^5$ and $R^{11}$ has the specific meaning given in the corresponding row of Table A.

Table 13:
Table 13 discloses 391 compounds of formula (IIIA) wherein $R^1$ is methyl, $R^2$ is isopropyl and each of the variables $R^3$, $R^5$ and $R^{11}$ has the specific meaning given in the corresponding row of Table A.

Table 14:
Table 14 discloses 391 compounds of formula (IIIA) wherein $R^1$ is methyl, $R^2$ is methyl and each of the variables $R^3$, $R^5$ and $R^{11}$ has the specific meaning given in the corresponding row of Table A.

Table 15:
Table 15 discloses 391 compounds of formula (IIIA) wherein $R^1$ is ethyl, $R^2$ is hydrogen and each of the variables $R^3$, $R^5$ and $R^{11}$ has the specific meaning given in the corresponding row of Table A.

Table 16:
Table 16 discloses 391 compounds of formula (IIIA) wherein $R^1$ is methyl, $R^2$ is hydrogen and each of the variables $R^3$, $R^5$ and $R^{11}$ has the specific meaning given in the corresponding row of Table A.

Table 17:
Table 17 discloses 391 compounds of formula (IIIA) wherein $R^1$ is isopropyl, $R^2$ is hydrogen and each of the variables $R^3$, $R^5$ and $R^{11}$ has the specific meaning given in the corresponding row of Table A.

Table 18:
Table 18 discloses 391 compounds of formula (IIIA) wherein $R^1$ and $R^2$ together form a four-membered alkylene bridge and each of the variables $R^3$, $R^5$ and $R^{11}$ has the specific meaning given in the corresponding row of Table A. For example, compound 18.1 has the following structure:

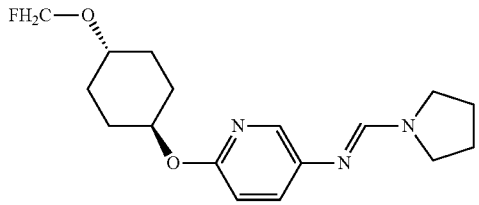

Table 19:
Table 19 discloses 391 compounds of formula (IVA) wherein $R^1$ is methyl, $R^2$ is ethyl and each of the variables $R^3$, $R^5$ and $R^{11}$ has the specific meaning given in the corresponding row of Table A. For example, compound 19.1 has the following structure:

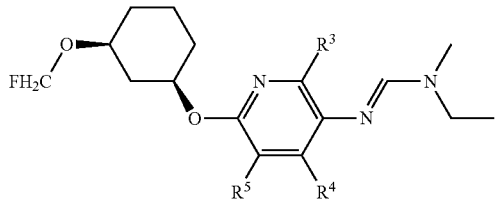

Table 20:
Table 20 discloses 391 compounds of formula (IVA) wherein $R^1$ is ethyl, $R^2$ is ethyl and each of the variables $R^3$, $R^5$ and $R^{11}$ has the specific meaning given in the corresponding row of Table A.

Table 21:
Table 21 discloses 391 compounds of formula (IVA) wherein $R^1$ is methyl, $R^2$ is cyclopropyl and each of the variables $R^3$, $R^5$ and $R^{11}$ has the specific meaning given in the corresponding row of Table A.

Table 22:
Table 22 discloses 391 compounds of formula (IVA) wherein $R^1$ is methyl, $R^2$ is isopropyl and each of the variables $R^3$, $R^5$ and $R^{11}$ has the specific meaning given in the corresponding row of Table A.

Table 23:
Table 23 discloses 391 compounds of formula (IVA) wherein $R^1$ is methyl, $R^2$ is methyl and each of the variables $R^3$, $R^5$ and $R^{11}$ has the specific meaning given in the corresponding row of Table A.

Table 24:
Table 24 discloses 391 compounds of formula (IVA) wherein $R^1$ is ethyl, $R^2$ is hydrogen and each of the variables $R^3$, $R^5$ and $R^{11}$ has the specific meaning given in the corresponding row of Table A.

Table 25:
Table 25 discloses 391 compounds of formula (IVA) wherein $R^1$ is methyl, $R^2$ is hydrogen and each of the variables $R^3$, $R^5$ and $R^{11}$ has the specific meaning given in the corresponding row of Table A.

Table 26:
Table 26 discloses 391 compounds of formula (IVA) wherein $R^1$ is isopropyl, $R^2$ is hydrogen and each of the variables $R^3$, $R^5$ and $R^{11}$ has the specific meaning given in the corresponding row of Table A.

Table 27:
Table 27 discloses 391 compounds of formula (IVA) wherein $R^1$ and $R^2$ together form a four-membered alkylene bridge and each of the variables $R^3$, $R^5$ and $R^{11}$ has the specific meaning given in the corresponding row of Table A. For example, compound 27.1 has the following structure:

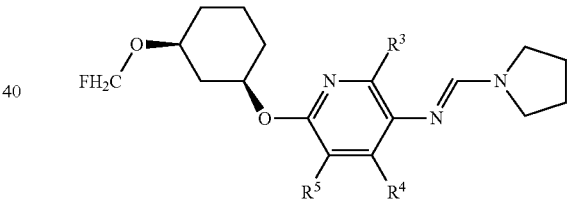

Table 28:
Table 28 discloses 391 compounds of formula (VA) wherein $R^1$ is methyl, $R^2$ is ethyl and each of the variables $R^3$, $R^5$ and $R^1$ has the specific meaning given in the corresponding row of Table A. For example, compound 28.1 has the following structure:

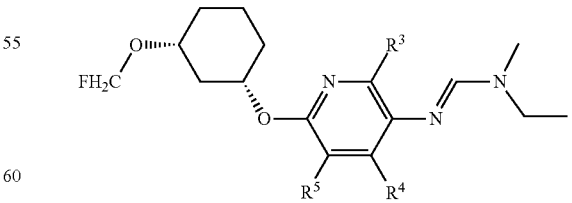

Table 29:
Table 29 discloses 391 compounds of formula (VA) wherein $R^1$ is ethyl, $R^2$ is ethyl and each of the variables $R^3$, $R^5$ and $R^{11}$ has the specific meaning given in the corresponding row of Table A.

Table 30:
Table 30 discloses 391 compounds of formula (VA) wherein $R^1$ is methyl, $R^2$ is cyclopropyl and each of the variables $R^3$, $R^5$ and $R^{11}$ has the specific meaning given in the corresponding row of Table A.

Table 31:
Table 31 discloses 391 compounds of formula (VA) wherein $R^1$ is methyl, $R^2$ is isopropyl and each of the variables $R^3$, $R^5$ and $R^{11}$ has the specific meaning given in the corresponding row of Table A.

Table 32:
Table 32 discloses 391 compounds of formula (VA) wherein $R^1$ is methyl, $R^2$ is methyl and each of the variables $R^3$, $R^5$ and $R^{11}$ has the specific meaning given in the corresponding row of Table A.

Table 33:
Table 33 discloses 391 compounds of formula (VA) wherein $R^1$ is ethyl, $R^2$ is hydrogen and each of the variables $R^3$, $R^5$ and $R^{11}$ has the specific meaning given in the corresponding row of Table A.

Table 34:
Table 34 discloses 391 compounds of formula (VA) wherein $R^1$ is methyl, $R^2$ is hydrogen and each of the variables $R^3$, $R^5$ and $R^{11}$ has the specific meaning given in the corresponding row of Table A.

Table 35:
Table 35 discloses 391 compounds of formula (VA) wherein $R^1$ is isopropyl, $R^2$ is hydrogen and each of the variables $R^3$, $R^5$ and $R^{11}$ has the specific meaning given in the corresponding row of Table A.

Table 36:
Table 36 discloses 391 compounds of formula (VA) wherein $R^1$ and $R^2$ together form a four-membered alkylene bridge and each of the variables $R^3$, $R^5$ and $R^{11}$ has the specific meaning given in the corresponding row of Table A. For example, compound 28.1 has the following structure:

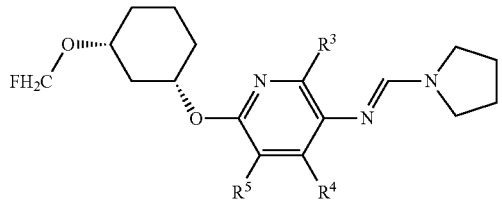

Table 37:
Table 37 discloses 391 compounds of formula (VIA) wherein $R^1$ is methyl, $R^2$ is ethyl and each of the variables $R^3$, $R^5$ and $R^{11}$ has the specific meaning given in the corresponding row of Table A. For example, compound 37.1 has the following structure:

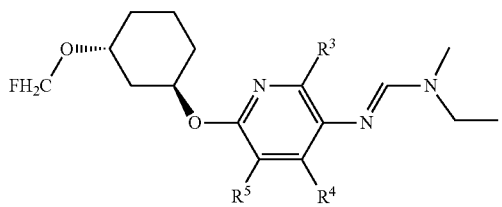

Table 38:
Table 38 discloses 391 compounds of formula (VIA) wherein $R^1$ is ethyl, $R^2$ is ethyl and each of the variables $R^3$, $R^5$ and $R^{11}$ has the specific meaning given in the corresponding row of Table A.

Table 39:
Table 39 discloses 391 compounds of formula (VIA) wherein $R^1$ is methyl, $R^2$ is cyclopropyl and each of the variables $R^3$, $R^5$ and $R^{11}$ has the specific meaning given in the corresponding row of Table A.

Table 40:
Table 40 discloses 391 compounds of formula (VIA) wherein $R^1$ is methyl, $R^2$ is isopropyl and each of the variables $R^3$, $R^5$ and $R^{11}$ has the specific meaning given in the corresponding row of Table A.

Table 41:
Table 41 discloses 391 compounds of formula (VIA) wherein $R^1$ is methyl, $R^2$ is methyl and each of the variables $R^3$, $R^5$ and $R^{11}$ has the specific meaning given in the corresponding row of Table A.

Table 42:
Table 42 discloses 391 compounds of formula (VIA) wherein $R^1$ is ethyl, $R^2$ is hydrogen and each of the variables $R^3$, $R^5$ and $R^{11}$ has the specific meaning given in the corresponding row of Table A.

Table 43:
Table 43 discloses 391 compounds of formula (VIA) wherein $R^1$ is methyl, $R^2$ is hydrogen and each of the variables $R^3$, $R^5$ and $R^{11}$ has the specific meaning given in the corresponding row of Table A.

Table 44:
Table 44 discloses 391 compounds of formula (VIA) wherein $R^1$ is isopropyl, $R^2$ is hydrogen and each of the variables $R^3$, $R^5$ and $R^{11}$ has the specific meaning given in the corresponding row of Table A.

Table 45:
Table 45 discloses 391 compounds of formula (VIA) wherein $R^1$ and $R^2$ together form a four-membered alkylene bridge and each of the variables $R^3$, $R^5$ and $R^{11}$ has the specific meaning given in the corresponding row of Table A. For example, compound 45.1 has the following structure:

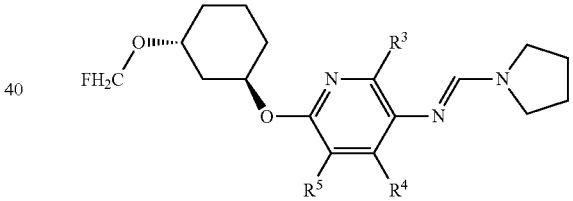

Table 46:
Table 46 discloses 391 compounds of formula (VIIA) wherein $R^1$ is methyl, $R^2$ is ethyl and each of the variables $R^3$, $R^5$ and $R^{11}$ has the specific meaning given in the corresponding row of Table A. For example, compound 46.1 has the following structure:

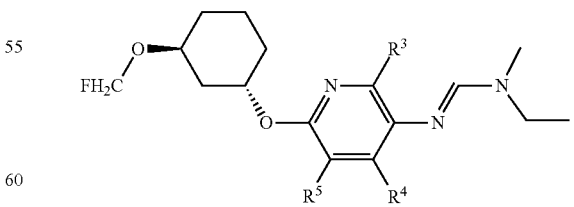

Table 47:
Table 47 discloses 391 compounds of formula (VIIA) wherein $R^1$ is ethyl, $R^2$ is ethyl and each of the variables $R^3$, $R^5$ and $R^{11}$ has the specific meaning given in the corresponding row of Table A.

Table 48:

Table 48 discloses 391 compounds of formula (VIIA) wherein $R^1$ is methyl, $R^2$ is cyclopropyl and each of the variables $R^3$, $R^5$ and $R^{11}$ has the specific meaning given in the corresponding row of Table A.

Table 49:

Table 49 discloses 391 compounds of formula (VIIA) wherein $R^1$ is methyl, $R^2$ is isopropyl and each of the variables $R^3$, $R^5$ and $R^{11}$ has the specific meaning given in the corresponding row of Table A.

Table 50:

Table 50 discloses 391 compounds of formula (VIIA) wherein $R^1$ is methyl, $R^2$ is methyl and each of the variables $R^3$, $R^5$ and $R^{11}$ has the specific meaning given in the corresponding row of Table A.

Table 51:

Table 51 discloses 391 compounds of formula (VIIA) wherein $R^1$ is ethyl, $R^2$ is hydrogen and each of the variables $R^3$, $R^5$ and $R^{11}$ has the specific meaning given in the corresponding row of Table A.

Table 52:

Table 52 discloses 391 compounds of formula (VIIA) wherein $R^1$ is methyl, $R^2$ is hydrogen and each of the variables $R^3$, $R^5$ and $R^{11}$ has the specific meaning given in the corresponding row of Table A.

Table 53:

Table 53 discloses 391 compounds of formula (VIIA) wherein $R^1$ is isopropyl, $R^2$ is hydrogen and each of the variables $R^3$, $R^5$ and $R^{11}$ has the specific meaning given in the corresponding row of Table A.

Table 54:

Table 54 discloses 391 compounds of formula (VIIA) wherein $R^1$ and $R^2$ together form a four-membered alkylene bridge and each of the variables $R^3$, $R^5$ and $R^{11}$ has the specific meaning given in the corresponding row of Table A. For example, compound 54.1 has the following structure:

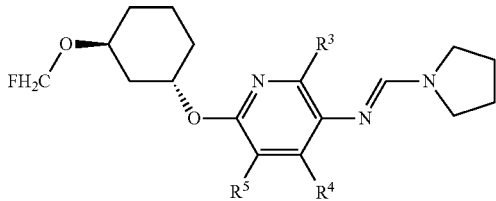

Compounds according to the invention may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile, improved physico-chemical properties, or increased biodegradability).

Compounds of formula I and fungicidal compositions containing them may be used to control plant diseases caused by a broad spectrum of fungal plant pathogens in the Basidiomycete, Ascomycete, Oomycete and/or Deuteromycete, Blasocladiomycete, Chrytidiomycete, Glomeromycete and/or Mucoromycete classes.

The invention therefore also relates to a method of controlling or preventing infestation of useful plants by phytopathogenic microorganisms, wherein a compound of formula (I) is applied as active ingredient to the plants, to parts thereof or the locus thereof.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The compounds of formula I can be used in the agricultural sector and related fields of use e.g. as active ingredients for controlling plant pests or on non-living materials for control of spoilage microorganisms or organisms potentially harmful to man.

The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants of different crops of useful plants, while at the same time protecting also those parts of the plants that grow later from phytopathogenic micro-organisms.

It is possible to use compounds of formula I as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

A preferred method of applying a compound of formula (I) is foliar application. The frequency of application and the rate of application will depend on the risk of infestation by the corresponding pathogen. However, the compounds of formula (I) may also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field.

It is also possible to use compounds of formula (I) as dressing agents for the treatment of plant propagation material, in particular of seeds and plant cuttings (e.g. rice), for the protection against fungal infections as well as against phytopathogenic fungi occurring in the soil.

The propagation material can be treated with a composition comprising a compound of formula I before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

Furthermore the compounds of formula (I) according to the invention may be used for controlling fungi in related areas, for example in the protection of technical materials, including wood and wood related technical products, in food storage or in hygiene management.

In addition, the invention could be used to protect non-living materials from fungal attack, e.g. lumber, wall boards and paint.

The compounds of formula I are for example, effective against Fungi and fungal vectors of disease as well as phytopathogenic bacteria and viruses. These pathogens may include:

Oomycetes, including *Phytophthora* diseases such as those caused by *Phytophthora capsici, Phytophthora infestans, Phytophthora sojae, Phytophthora fragariae, Phytophthora nicotianae, Phytophthora cinnamomi, Phytophthora citricola, Phytophthora citrophthora* and *Phytophthora erythroseptica; Pythium* diseases such as those caused by *Pythium aphanidermatum, Pythium arrhenomanes, Pythium graminicola, Pythium irregulare* and *Pythium ultimum;* diseases caused by Peronosporales such as *Peronospora destructor, Peronospora parasitica, Plasmopara viticola, Plasmopara halstedii, Pseudoperonospora cubensis, Albugo candida, Sclerophthora macrospora* and *Bremia lactucae;* and others such as *Aphanomyces cochlioides, Labyrinthula zosterae, Peronosclerospora sorghi* and *Sclerospora graminicola.*

Ascomycetes, including blotch, spot, blast or blight diseases and/or rots for example those caused by Pleosporales such as *Stemphylium solani, Stagonospora tainanensis, Spilocaea oleaginea, Setosphaeria turcica, Pyrenochaeta lycoperisici, Pleospora herbarum, Phoma destructiva, Phaeosphaeria herpotrichoides, Phaeocryptocus gaeumannii, Ophiosphaerella graminicola, Ophiobolus graminis, Leptosphaeria maculans, Hendersonia creberrima, Helminthosporium triticirepentis, Setosphaeria turcica, Drechslera glycines, Didymella bryoniae, Cycloconium oleagineum, Corynespora cassiicola, Cochliobolus sativus, Bipolaris cactivora, Venturia inaequalis, Pyrenophora teres, Pyrenophora tritici-repentis, Alternaria alternata, Alternaria brassicicola, Alternaria solani and Alternaria tomatophila,* Capnodiales such as *Septoria tritici, Septoria nodorum, Septoria glycines, Cercospora arachidicola, Cercospora sojina, Cercospora zeae-maydis, Cercosporella capsellae* and *Cercosporella herpotrichoides, Cladosporium carpophilum, Cladosporium effusum, Passalora fulva, Cladosporium oxysporum, Dothistroma septosporum, Isariopsis clavispora, Mycosphaerella fijiensis, Mycosphaerella graminicola, Mycovellosiella koepkeii, Phaeoisariopsis bataticola, Pseudocercospora vitis, Pseudocercosporella herpotrichoides, Ramularia beticola, Ramularia collo-cygni,* Magnaporthales such as *Gaeumannomyces graminis, Magnaporthe grisea, Pyricularia oryzae,* Diaporthales such as *Anisogramma anomala, Apiognomonia errabunda, Cytospora platani, Diaporthe phaseolorum, Discula destructiva, Gnomonia fructicola, Greeneria uvicola, Melanconium juglandinum, Phomopsis viticola, Sirococcus clavigignenti-juglandacearum, Tubakia dryina, Dicarpella* spp., *Valsa ceratosperma,* and others such as *Actinothyrium graminis, Ascochyta pisi, Aspergillus flavus, Aspergillus fumigatus, Aspergillus nidulans, Asperisporium caricae, Blumeriella jaapii, Candida* spp., *Capnodium ramosum, Cephaloascus* spp., *Cephalosporium gramineum, Ceratocystis paradoxa, Chaetomium* spp., *Hymenoscyphus pseudoalbidus, Coccidioides* spp., *Cylindrosporium padi, Diplocarpon malae, Drepanopeziza campestris, Elsinoe ampelina, Epicoccum nigrum, Epidermophyton* spp., *Eutypa lata, Geotrichum candidum, Gibellina cerealis, Gloeocercospora sorghi, Gloeodes pomigena, Gloeosporium perennans; Gloeotinia temulenta, Griphospaeria corticola, Kabatiella lini, Leptographium microsporum, Leptosphaerulinia crassiasca, Lophodermium seditiosum, Marssonina graminicola, Microdochium nivale, Monilinia fructicola, Monographella albescens, Monosporascus cannonballus, Naemacyclus* spp., *Ophiostoma novo-ulmi, Paracoccidioides brasiliensis, Penicillium expansum, Pestalotia rhododendri, Petriellidium* spp., *Pezicula* spp., *Phialophora gregata, Phyllachora pomigena, Phymatotrichum omnivora, Physalospora abdita, Plectosporium tabacinum, Polyscytalum pustulans, Pseudopeziza medicaginis, Pyrenopeziza brassicae, Ramulispora sorghi, Rhabdocline pseudotsugae, Rhynchosporium secalis, Sacrocladium oryzae, Scedosporium* spp., *Schizothyrium pomi, Sclerotinia sclerotiorum, Sclerotinia minor Sclerotium* spp., *Typhula ishikariensis, Seimatosporium mariae, Lepteutypa cupressi, Septocyta ruborum, Sphaceloma perseae, Sporonema phacidioides, Stigmina palmivora, Tapesia yallundae, Taphrina bullata, Thielviopsis basicola, Trichoseptoria fructigena, Zygophiala jamaicensis;* powdery mildew diseases for example those caused by Erysiphales such as *Blumeria graminis, Erysiphe polygoni, Uncinula necator, Sphaerotheca fuligena, Podosphaera leucotricha, Podospaera macularis Golovinomyces cichoracearum, Leveillula taurica, Microsphaera diffusa, Oidiopsis gossypii, Phyllactinia guttata* and *Oidium arachidis;* molds for example those caused by Botryosphaeriales such as *Dothiorella aromatica, Diplodia seriata, Guignardia bidwellii, Botrytis cinerea, Botryotinia allii, Botryotinia fabae, Fusicoccum amygdali, Lasiodiplodia theobromae, Macrophoma theicola, Macrophomina phaseolina, Phyllosticta cucurbitacearum;* anthracnoses for example those caused by Glommerelales such as *Colletotrichum gloeosporioides, Colletotrichum lagenarium, Colletotrichum gossypii, Glomerella cingulata,* and *Colletotrichum graminicola;* and wilts or blights for example those caused by Hypocreales such as *Acremonium strictum, Claviceps purpurea, Fusarium culmorum, Fusarium graminearum, Fusarium virguliforme, Fusarium oxysporum, Fusarium subglutinans, Fusarium oxysporum* f. sp. *cubense, Gerlachia nivale, Gibberella fujikuroi, Gibberella zeae, Gliocladium* spp., *Myrothecium verrucaria, Nectria ramulariae, Trichoderma viride, Trichothecium roseum,* and *Verticillium theobromae.*

Basidiomycetes, including smuts for example those caused by Ustilaginales such as *Ustilaginoidea virens, Ustilago nuda, Ustilago tritici, Ustilago zeae,* rusts for example those caused by Pucciniales such as *Cerotelium fici, Chrysomyxa arctostaphyli, Coleosporium ipomoeae, Hemileia vastatrix, Puccinia arachidis, Puccinia cacabata, Puccinia graminis, Puccinia recondita, Puccinia sorghi, Puccinia hordei, Puccinia striiformis* f. sp. *Hordei, Puccinia striiformis* f. sp. *Secalis, Pucciniastrum coryli,* or Uredinales such as *Cronartium ribicola, Gymnosporangium juniperi-viginianae, Melampsora medusae, Phakopsora pachyrhizi, Phragmidium mucronatum, Physopella ampelosidis, Tranzschelia discolor* and *Uromyces viciae-fabae;* and other rots and diseases such as those caused by *Cryptococcus* spp., *Exobasidium vexans, Marasmiellus inoderma, Mycena* spp., *Sphacelotheca reiliana, Typhula ishikariensis, Urocystis agropyri, Itersonilia perplexans, Corticium invisum, Laetisania fuciformis, Waitea circinata, Rhizoctonia solani, Thanetephorus cucurmeris, Entyloma dahliae, Entylomella microspor, Neovossia moliniae* and *Tilletia caries.*

Blastocladiomycetes, such as *Physoderma maydis.*

Mucoromycetes, such as *Choanephora cucurbitarum; Mucor* spp.; *Rhizopus arrhizus,*

As well as diseases caused by other species and genera closely related to those listed above.

In addition to their fungicidal activity, the compounds and compositions comprising them may also have activity against bacteria such as *Erwinia amylovora, Erwinia caratovora, Xanthomonas campestris, Pseudomonas syringae, Streptomyces* scabies and other related species as well as certain protozoa.

Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®.

Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as active ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

A formulation, i.e. a composition comprising the compound of formula (I) and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula (I), 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Normally, in the management of a crop a grower would use one or more other agronomic chemicals in addition to the compound of the present invention. Examples of agronomic chemicals include insecticides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection, as well as plant nutrients and plant fertilizers.

Accordingly, the present invention provides a composition comprising a compound of formula (I) according to the present invention together with one or more pesticides, plant nutrients or plant fertilizers. The combination may also encompass specific plant traits incorporated into the plant using any means, for example conventional breeding or genetic modification. Such compositions may also contain one or more inert carriers as described above.

The invention also provides for the use of provides a composition comprising a compound of formula (I) according to the present invention together with one or more pesticides, plant nutrients or plant fertilizers. The combination may also encompass specific plant traits incorporated into the plant using any means, for example conventional breeding or genetic modification.

Suitable examples of plant nutrients or plant fertilizers are calcium sulfate ($CaSO_4$), calcium nitrate ($Ca(NO_3)_2.4H_2O$), calcium carbonate ($CaCO_3$), potassium nitrate ($KNO_3$), magnesium sulfate ($MgSO_4$), potassium hydrogen phosphate ($KH_2PO_4$), manganese sulfate ($MnSO_4$), copper sulfate ($CuSO_4$), zinc sulfate ($ZnSO_4$), nickel chloride ($NiCl_2$), cobalt sulfate ($CoSO_4$), potassium hydroxide (KOH), sodium chloride (NaCl), boric acid ($H_3BO_3$) and metal salts thereof ($Na_2MoO_4$). The nutrients may be present in an amount of 5% to 50% by weight, preferably of 10% to 25% by weight or of 15% to 20% by weight each. Preferred additional nutrients are urea ($(NH_2)_2CO$), melamine ($C_3H_6N_6$), potassium oxide ($K_2O$), and inorganic nitrates. The most preferred additional plant nutrient is potassium oxide. Where the preferred additional nutrient is urea, it is present in an amount of generally 1% to 20% by weight, preferably 2% to 10% by weight or of 3% to 7% by weight.

Suitable examples of pesticides are 1,2,4-thiadiazoles, 2,6-dinitroanilines, acylalanines, aliphatic nitrogenous compounds, amidines, aminopyrimidinols, anilides, anilino-pyrimidines, anthraquinones, antibiotics, aryl-phenylketones, benzamides, benzene-sulfonamides, benzimidazoles, benzothiazoles, benzothiodiazoles, benzothiophenes, benzoylpyridines, benzthiadiazoles, benzylcarbamates, butylamines, carbamates, carboxamides, carpropamids, chloronitriles, cinnamic acid amides, copper containing compounds, cyanoacetamideoximes, cyanoacrylates, cyanoimidazoles, cyanomethylene-thiazolidines, dicarbonitriles, dicarboxamides, dicarboximides, dimethylsulphamates, dinitrophenol carbonates, dinitrophenysl, dinitrophenyl crotonates, diphenyl phosphates, dithiino compounds, dithiocarbamates, dithioethers, dithiolanes, ethyl-amino-thiazole carboxamides, ethyl-phosphonates, furan carboxamides, glucopyranosyls, glucopyranoxyls, glutaronitriles, guanidines, herbicides/plant growth regulators, hexopyranosyl antibiotics, hydroxy (2-amino)pyrimidines, hydroxyanilides, hydroxyisoxazoles, imidazoles, imidazolinones, insecticides/plant growth regulators, isobenzofuranones, isoxazolidinyl-pyridines, isoxazolines, maleimides, mandelic acid amides, mectin derivatives, morpholines, norpholines, n-phenyl carbamates, organotin compounds, oxathiin carboxamides, oxazoles, oxazolidine-diones, phenols, phenoxy quinolines, phenylacetamides, phenylamides, phenylbenzamides, phenyl-oxoethyl-thiophenes amides, phenylpyrroles, phenylureas, phosphorothiolates, phosphorus acids, phthalamic acids, phthalimides, picolinamides, piperazines, piperidines, plant extracts, polyoxins, propionamides, pthalimides, pyrazole-4-carboxamides, pyrazolinones, pyridazinones, pyridines, pyridine carboxamides, pyridinyl-ethyl benzamides, pyrimidinamines, pyrimidines, pyrimidine-amines, pyrimidionehydrazone, pyrrolidines, pyrrolquinoliones, quinazolinones, quinolines, quinoline derivatives, quinoline-7-carboxylic acids, quinoxalines, spiroketalamines, strobilurins, sulfamoyl triazoles, sulphamides, tetrazolyloximes, thiadiazines, thiadiazole carboxamides, thiazole carboxanides, thiocyanates, thiophene carboxamides, toluamides, triazines, triazobenthiazoles, triazoles, triazole-thiones, triazolo-pyrimidylamine, valinamide carbamates, ammonium methyl phosphonates, arsenic-containing compounds, benyimidazolylcarbamates, carbonitriles, carboxanilides, carboximidamides, carboxylic phenylamides, diphenyl pyridines, furanilides, hydrazine carboxamides, imidazoline acetates, isophthalates, isoxazolones, mercury salts, organomercury compounds, organophosphates, oxazolidinediones, pentylsulfonyl benzenes, phenyl benzamides, phosphonothionates, phosphorothioates, pyridyl carboxamides, pyridyl furfuryl ethers, pyridyl methyl ethers, SDHIs, thiadiazinanethiones, thiazolidines.

The following non-limiting Examples illustrate the above-described invention in greater detail without limiting it. Those skilled in the art will promptly recognise appropriate variations from the procedures both as to reactants and as to reaction conditions and techniques. All references mentioned herein are incorporated by reference in their entirety.

FORMULATION EXAMPLES

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

Emulsifiable Concentrate

| | |
|---|---|
| active ingredient [compound of formula (I)] | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| Active ingredient [compound of formula (I)] | 15% |
|---|---|
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| Active ingredient [compound of formula (I)] | 8% |
|---|---|
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| active ingredient [compound of formula (I)] | 40% |
|---|---|
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| active ingredient [compound of formula (I)] | 40% |
|---|---|
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula I are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

SYNTHETIC EXAMPLES

Using techniques described below and in WO 12/146125 (pp. 370-378) together with further techniques known to the person skilled in the art, for example as found in WO 08/101682 (pp. 22-33), compounds of formula (I) may be prepared Preparation of 3-(difluoromethoxy)cyclohexanol

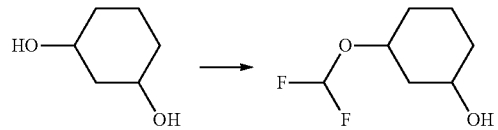 [SMILES: OC1CCCC(O)C1 ; OC1CCCC(OC(F)F)C1]

To a solution of cyclohexane-1,3-diol (2.30 g) in of $CH_3CN$ (50 mL), $FSO_2CF_2COOH$ (1.2 equiv.) was added dropwise at 50° C. for 1 hour. After stirring for 10 min, the mixture was poured into water, extracted with $CH_2Cl_2$, dried over $Na_2SO_4$, evaporated to dryness and further purified by chromatography on silica gel to provide 1.2 g of the title compound in 36% yield.

$H^1$ NMR (400 MHz, $CDCl_3$): δ 6.65 (t, 0.5H), 6.64 (t, 0.5H), 4.60 (m, 1H), 4.35 (m, 0.5H), 3.80 (m, 0.5H), 3.70 (m, 0.5H), 3.45 (m, 0.5H), 2.10-0.85 (m, 8H).

$F^{19}$ NMR (376.5 MHz, $CDCl_3$): δ −66.7 (s), −66.6 (s).

Preparation of N'-[5-bromo-6-[3-(difluoromethoxy) cyclohexoxy]-2-methyl-3-pyridyl]-N-ethyl-N-methyl-formamidine

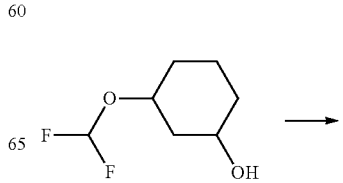

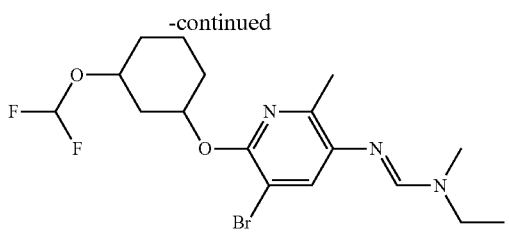

To a solution of 3-(difluoromethoxy)cyclohexanol (358 mg, 2.16 mmol), triphenylphosphine (1 equiv.) and N'-(5-bromo-6-hydroxy-2-methyl-3-pyridyl)-N-ethyl-N-methyl-formamidine (0.9 equiv) in THF (50 mL), diisopropyl azodicarboxylate (1.3 equiv.) was added at 60° C. After stirring for 12 hours, the mixture was concentrated to dryness and purified by chromatography on silica gel to isolate the title compound separately as 110 mg of the cis-isomer (14% yield) and 130 mg of the trans-isomer (17% yield).

H$^1$ NMR (400 MHz, CDCl$_3$; cis-isomer): δ 7.40 (broad s, 1H), 7.21 (s, 1H), 6.23 (t, 1H), 5.41 (m, 1H), 4.52 (m, 1H), 3.31 (m, 2H), 2.98 (s, 3H), 2.83 (s, 3H), 2.14 (m, 1H), 1.92 (m, 1H), 1.82 (m, 2H), 1.68 (m, 4H), 1.21 (t, 3H).

F$^{19}$ NMR (376.5 MHz, CDCl$_3$): δ −68.5 (s).

H$^1$ NMR (400 MHz, CDCl$_3$; trans-isomer): δ 7.37 (broad s, 1H), 7.24 (s, 1H), 6.21 (t, 1H), 4.98 (m, 1H), 4.18 (m, 1H), 3.20 (m, 2H), 3.00 (s, 3H), 2.50 (m, 1H), 2.34 (s, 3H), 2.10 (m, 1H), 2.02 (m, 1H), 1.83 (m, 1H), 1.61 (m, 2H), 1.38 (m, 2H), 1.20 (t, 3H).

F$^{19}$ NMR (376.5 MHz, CDCl$_3$): δ −69.5 (s).

Preparation of 4-(difluoromethoxy)cyclohexanol

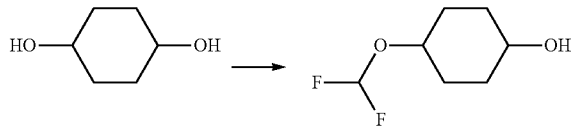 [SMILES: OC1CCC(O)CC1 ; OC1CCC(OC(F)F)CC1]

To the mixture of cyclohexane-1,4-diol (11.6 g, 0.1 mol) and Na$_2$SO$_4$ (7.1 g, 0.05 Mol) in CH$_3$CN (120 mL), FSO$_2$CF$_2$COOH (21.36 g, 0.12 mol) in CH$_3$CN (30 mL) was added dropwise over a period of 1 hour to maintain the temperature at 40 to 45° C. After addition, the liquid was poured into 200 mL of water, extracted with DCM (100 mL*3). The combined extracts was dried over Na$_2$SO$_4$, evaporated, and finally purified by flash column chromatography on silica to give 6.2 g of the titled compound in 37% yield. Note: 4-(difluoromethoxy)cyclohexanol is quite unstable. It is best to use this compound to the next step reaction immediately after simple purification.

H$^1$ NMR (400 MHz, CDCl$_3$): δ 6.21 (t, 0.5H), 6.19 (t, 0.5H), 4.23 (m, 1H), 3.73 (m, 1H), 1.95 (m, 2H), 1.70 (m, 2H), 1.60 (m, 2H), 1.40 (m, 2H).

F$^{19}$ NMR (376.5 MHz, CDCl$_3$): δ −80.9 (s), −80.8 (s).

Preparation of cis-N'-[5-bromo-6-[4-(difluoromethoxy)cyclohexoxy]-2-methyl-3-pyridyl]-N-ethyl-N-methylformamidine and racemic N'-[5-bromo-6-[4-(difluoromethoxy)cyclohexoxy]-2-methyl-3-pyridyl]-N-ethyl-N-methylformamidine

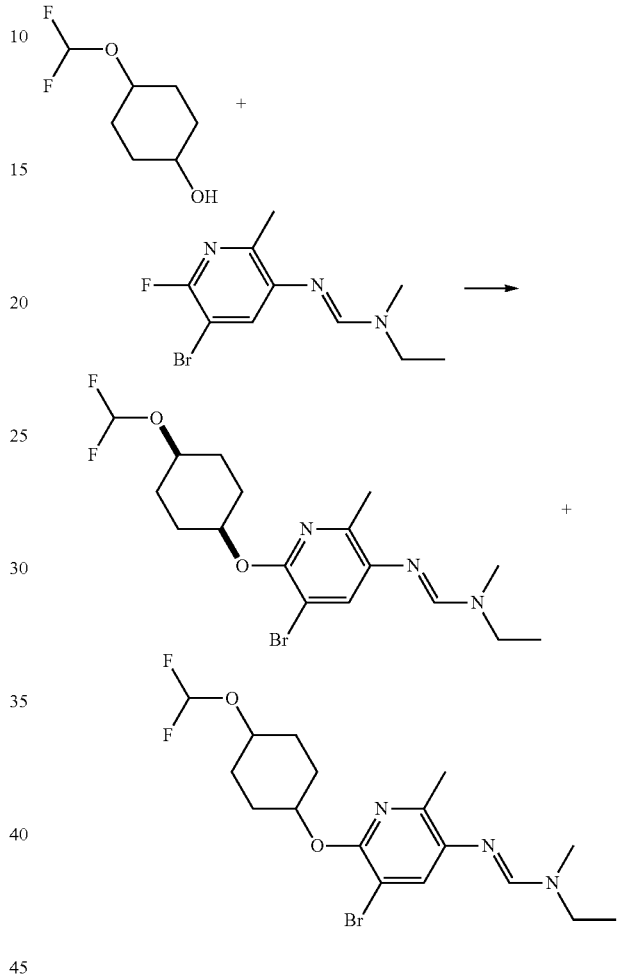

Solid KOH (3.92 g, 70 mmol) was added to a solution of N'-(5-bromo-6-fluoro-2-methyl-3-pyridyl)-N-ethyl-N-methyl-formamidine (5.48 g, 20 mmol), 4-(difluoromethoxy)cyclohexanol (3.98 g, 24 mmol) and 18-crown-6 (1.05 g, 4 mmol) in 80 mL toluene. The mixture was heated at 90° C. for 18 hours under nitrogen atmosphere. The reaction was cooled to 25° C. then the reaction mixture was poured into 80 mL of ice water, extracted with EtOAc (50 mL*3). The combined extracts were dried over Na$_2$SO$_4$, concentrated at reduced pressure, and purified by column chromatography on silica to give 1.0 g of the titled compound and 1.0 g of the racemate mixture of N'-[5-bromo-6-[4-(difluoromethoxy)cyclohexoxy]-2-methyl-3-pyridyl]-N-ethyl-N-methylformamidine in 12% yield.

H$^1$ NMR (400 MHz, CDCl$_3$): δ 7.37 (broad s, 1H), 7.21 (s, 1H), 6.21 (t, 1H), 5.11 (brs, 1H), 4.36 (m, 1H), 3.30 (m, 2H), 3.00 (s, 3H), 2.97 (s, 3H), 2.35 (s, 3H), 2.05 (m, 4H), 1.68 (m, 4H), 1.17 (t, 3H).

F$^{19}$ NMR (376.5 MHz, CDCl$_3$ δ ppm): −76.3.5 (s).

Preparation of trans-N'-[5-bromo-6-[4-(difluoromethoxy)cyclohexoxy]-2-methyl-3-pyridyl]-N-ethyl-N-methylformamidine

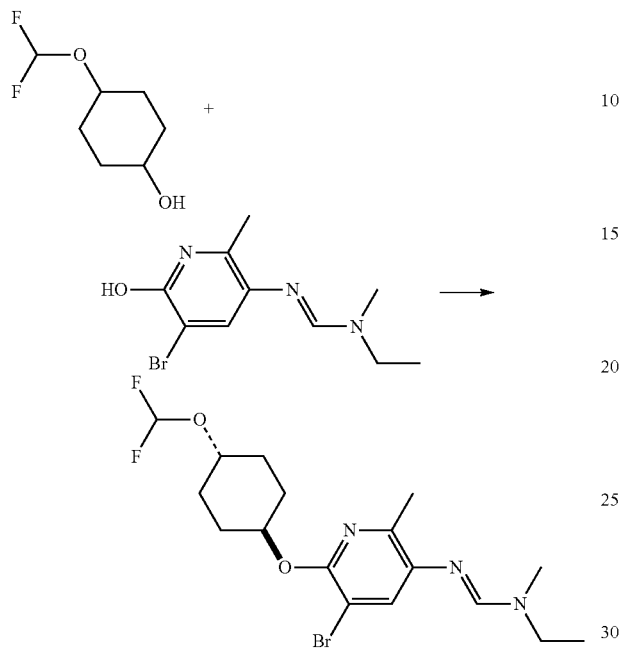

To a solution of 4-(difluoromethoxy)cyclohexanol (680 mg), triphenylphosphine (1.3 equiv) and N'-(5-bromo-hydroxy-2-methyl-3-pyridyl)-N-ethyl-N-methyl-formamidine (1 equiv.) in THF (30 mL) was added at diisopropyl azodicarboxylate (1.3 equiv.) at 65° C. After stirring for 18 h, the mixture was cooled 25° C. and concentrated to dryness. The resulting crude residue was purified by column chromatography on silica gel to provide 400 mg of the title compound in 25% yield.

$H^1$ NMR (400 MHz, $CDCl_3$): δ 7.40 (broad s, 1H), 7.23 (s, 1H), 6.26 (t, 1H), 5.16 (m, 1H), 4.22 (m, 1H), 3.35 (m, 2H), 2.98 (s, 3H), 2.34 (s, 3H), 1.98 (m, 4H), 1.76 (m, 2H), 1.67 (m, 2H), 1.18 (m, 3H).

$F^{19}$ NMR (376.5 MHz, $CDCl_3$): δ −80.6 (s).

Preparation of N'-(5-cyano-6-hydroxy-2-methyl-3-pyridyl)-N-ethyl-N-methyl-formamidine

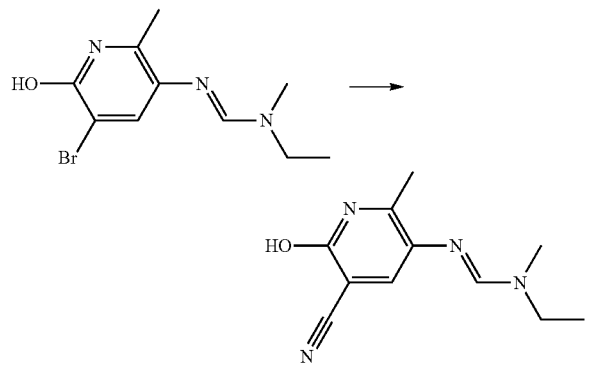

N'-(5-bromo-6-hydroxy-2-methyl-3-pyridyl)-N-ethyl-N-methyl-formamidine (10.00 g) was dissolved in dry DMF (33 mL) to give a yellow/orange solution which was degassed for 5 min by bubbling argon. $Zn(CN)_2$ (1.1 equiv.) and $Pd(PPh)_4$ (0.20 equiv.) were introduced and the orange mixture was stirred at 120° C. overnight. The reaction mixture was cooled to 25° C., diluted with $CH_2Cl_2$ and washed with saturated $NaHCO_3$ aqueous solution, water, dried over $Na_2SO_4$, filtered and concentrated to dryness. The crude residue was taken up in warm diethyl ether and then cooling slowly to −10° C. The brown suspension was filtered, washed with cold diethyl ether, and dried to provide 7.1 g of the title compound as a yellow solid in 88% yield.

$H^1$ NMR (400 MHz, $CDCl_3$): δ 13.80 (brs, 1H), 7.55 (s, 1H), 7.45 (m, 1H), 3.50 (m, 1H), 3.35 (m, 1H), 3.03 (s, 3H), 2.51 (s, 3H), 1.22 (m, 3H).

Preparation of trans N'-[5-cyano-6-[4-(difluoromethoxy)cyclohexoxy]-2-methyl-3-pyridyl]-N-ethyl-N-methyl-formamidine

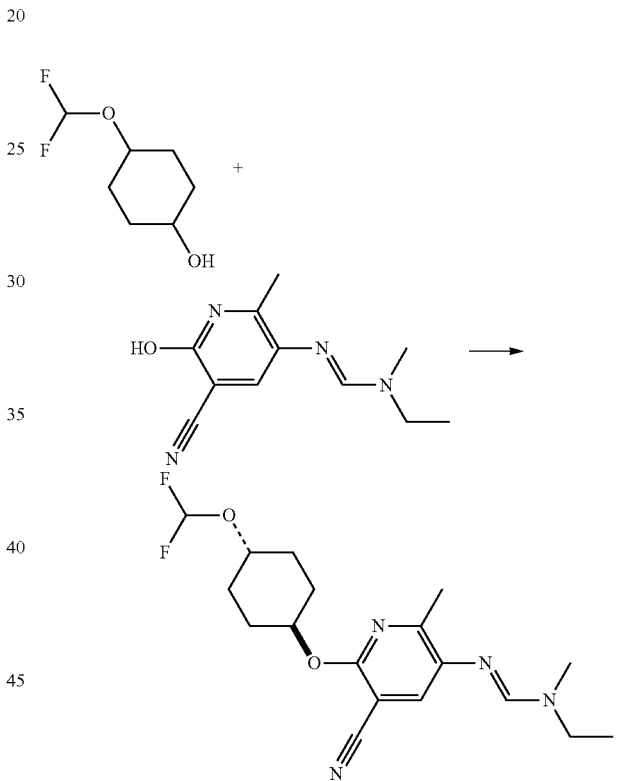

To a solution of N'-(5-cyano-hydroxy-2-methyl-3-pyridyl)-N-ethyl-N-methyl-formamidine (436 mg, 2 mmol), triphenylphosphine (786 mg, 3 mmol) and 4-(difluoromethoxy)cyclohexanol (664 mg, 4 mmol) in THF (20 mL), diisopropylazodicarboxylate (606 mg, 35 mmol) was added 60° C. After stirring for 12 h, the mixture was cooled to 25° C., concentrated to dryness, and the crude residue was purified by chromatography on silica gel to give 120 mg of the title compound in 16% yield.

$H^1$ NMR (400 MHz, $CDCl_3$): δ 7.43 (brs, 1H), 7.20 (s, 1H), 5.21 (m, 1H), 4.29 (m, 1H), 3.50 (brs, 1H), 3.35 (brs, 1H), 3.02 (s, 3H), 2.45 (s, 3H), 2.11 (m, 4H), 1.73 (m, 4H), 1.21 (m, 3H).

This table gives analytical data for compounds of formula (I) prepared using techniques described below and in WO 12/146125 (pp. 370-378) together with further techniques known to the person skilled in the art, for example as found in WO 08/101682 (pp. 22-33)

TABLE 55

| Compound No. | Name | Structure | R$_t$ (min); MS-ESI (m/z; (M + H)$^+$) |
|---|---|---|---|
| 55.001 | cis-N'-[5-bromo-6-[4-(difluoromethoxy)cyclohexoxy]-2-methyl-3-pyridyl]-N-ethyl-N-methyl-formamidine | 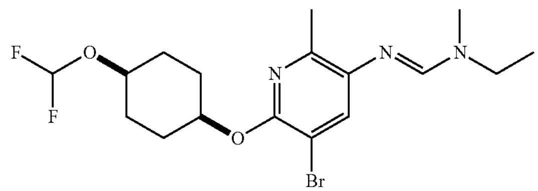 | 11.8 min.; 420, 422 |
| 55.002 | trans-N'-[5-bromo-6-[4-(difluoromethoxy)cyclohexoxy]-2-methyl-3-pyridyl]-N-ethyl-N-methyl-formamidine | 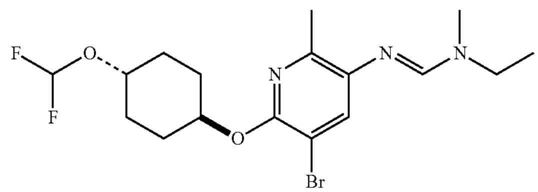 | 12.0 min.; 420, 422 |
| 55.003 | cis-N'-[5-cyano-6-[4-(difluoromethoxy)cyclohexoxy]-2-methyl-3-pyridyl]-N-ethyl-N-methyl-formamidine | 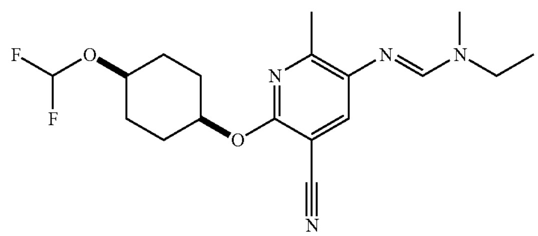 | 10.5 min.; 367 |
| 55.004 | trans-N'-[5-cyano-6-[4-(difluoromethoxy)cyclohexoxy]-2-methyl-3-pyridyl]-N-ethyl-N-methyl-formamidine | 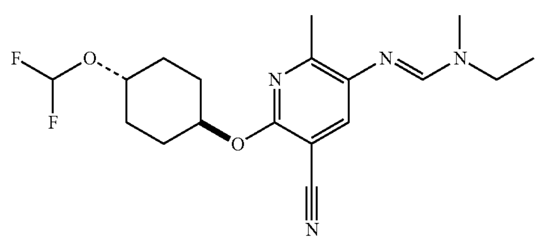 | 10.9 min.; 367 |
| 55.005 | cis-N'-[6-[4-(difluoromethoxy)cyclohexoxy]-2-methyl-3-pyridyl]-N-ethyl-N-methyl-formamidine | 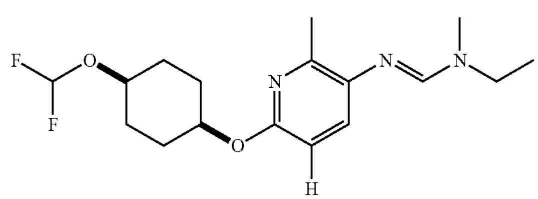 | 10.3 min.; 342 |
| 55.006 | trans-N'-[6-[4-(difluoromethoxy)cyclohexoxy]-2-methyl-3-pyridyl]-N-ethyl-N-methyl-formamidine | 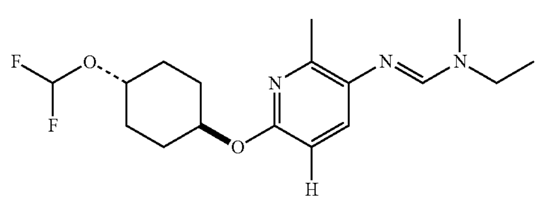 | 15.8 min.; 342 |
| 55.007 | cis-N'-[6-[4-(difluoromethoxy)cyclohexoxy]-2,5-dimethyl-3-pyridyl]-N-ethyl-N-methyl-formamidine | 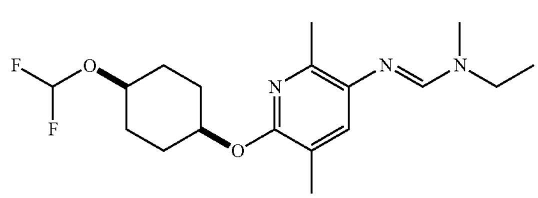 | 11.4 min.; 356 |

TABLE 55-continued

| Compound No. | Name | Structure | $R_t$ (min); MS-ESI (m/z; (M + H)+) |
|---|---|---|---|
| 55.008 | trans-N'-[6-[4-(difluoromethoxy)cyclohexoxy]-2,5-dimethyl-3-pyridyl]-N-ethyl-N-methyl-formamidine | 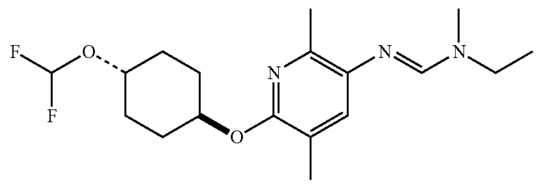 | 15.7 min.; 356 |
| 55.009 | cis-N'-[5-bromo-6-[3-(difluoromethoxy)cyclohexoxy]-2-methyl-3-pyridyl]-N-ethyl-N-methyl-formamidine | 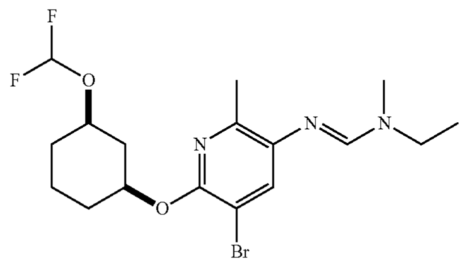 [SMILES: CCN(C)/C=N/c1cc(Br)c(O[C@H]2CCC[C@@H](OC(F)F)C2)nc1C] | 11.6 min.; 420, 422 |
| 55.010 | trans-N'-[5-bromo-6-[3-(difluoromethoxy)cyclohexoxy]-2-methyl-3-pyridyl]-N-ethyl-N-methyl-formamidine | 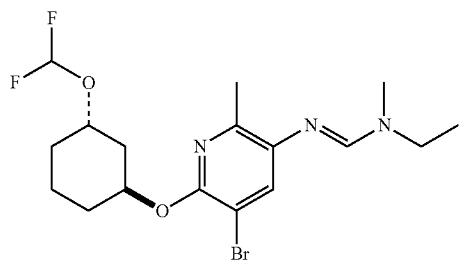 [SMILES: CCN(C)/C=N/c1cc(Br)c(O[C@H]2CCC[C@H](OC(F)F)C2)nc1C] | 11.8 min.; 420, 422 |
| 55.011 | N'-[5-bromo-6-[4-(difluoromethoxy)cyclohexoxy]-2-methyl-3-pyridyl]-N-ethyl-N-methyl-formamidine | 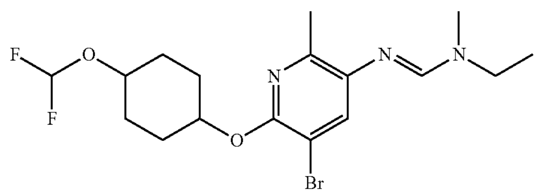 [SMILES: CCN(C)/C=N/c1cc(Br)c(OC2CCC(OC(F)F)CC2)nc1C] | 11.9 min.; 420, 422 |

Analytical Methods Used (Method a and Method B):

Mass spectra were recorded on a Mass Spectrometer from Shimadzu (SQD or ZQ Single quadrupole mass spectrometer) equipped with an electrospray source (Polarity: positive or negative ions, Capillary: 1.5 kV, Cone range: unknown, Extractor: 5.00 V, Source Temperature: 200° C., Desolvation Temperature: 250° C., Cone Gas Flow: 90 L/Hr, Desolvation Gas Flow: 90 L/Hr, Mass range: 50 to 900 Da) and an SPD-20A from LC from Shimadzu: Solvent degasser, binary pump, heated column compartment and ultraviolet detector. Column: Diamonsil C18 (2) 5 u 150*4.6 mm, Temp: 40° C., SPD-20A Wavelength range (nm): 210 to 500, Solvent Gradient: A=water+0.1% $F_3CCOOH$, B=Acetonitrile+0.1% $F_3CCOOH$; Gradient: 0 min 10% B, 90% A; 15 min 100% B; Flow 1.00 (ml/min)

BIOLOGICAL EXAMPLES

*Blumeria graminis* f. sp. *tritici* (*Erysiphe graminis* f. sp. *tritici*)/Wheat/Leaf Disc Preventative (Powdery Mildew on Wheat)

Wheat leaf segments cv. Kanzler were placed on agar in a multiwell plate (24-well format) and sprayed with the formulated test compound diluted in water. The leaf disks were inoculated by shaking powdery mildew infected plants above the test plates 1 day after application. The inoculated leaf disks were incubated at 20° C. and 60% rh under a light regime of 24 h darkness followed by 12 h light/12 h darkness in a climate chamber and the activity of a compound was assessed as percent disease control compared to untreated when an appropriate level of disease damage appears on untreated check leaf segments (6-8 days after application).

The following compounds gave at 200 ppm give at least 80% disease control in this test when compared to untreated control leaf disks under the same conditions, which show extensive disease development:

55.001, 55.002, 55.003, 55.004, 55.005, 55.006, 55.007, 55.008, 55.009, 55.010, 55.011

*Puccinia recondita* f. sp. *tritici*/Wheat/Leaf Disc Preventative (Brown Rust)

Wheat leaf segments cv. Kanzler were placed on agar in multiwell plates (24-well format) and sprayed with the formulated test compound diluted in water. The leaf disks were inoculated with a spore suspension of the fungus 1 day after application. The inoculated leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (7-9 days after application).

The following compounds gave at 200 ppm gave at least 80% disease control in this test when compared to untreated control leaf disks under the same conditions, which show extensive disease development:

55.001, 55.002, 55.003, 55.004, 55.005, 55.006, 55.007, 55.008, 55.009, 55.010, 55.011

*Puccinia recondita* f. sp. *tritici*/Wheat/Leaf Disc Curative (Brown Rust)

Wheat leaf segments cv. Kanzler are placed on agar in multiwell plates (24-well format). The leaf segments are inoculated with a spore suspension of the fungus. Plates were stored in darkness at 19° C. and 75% rh. The formulated test compound diluted in water was applied 1 day after inoculation. The leaf segments were incubated at 19° C. and 75% rh under a light regime of 12 h light/12 h darkness in a climate cabinet and the activity of a compound was assessed as percent disease control compared to untreated when an appropriate level of disease damage appears in untreated check leaf segments (6-8 days after application).

The following compounds gave at 200 ppm gave at least 80% disease control in this test when compared to untreated control leaf disks under the same conditions, which show extensive disease development:

55.001, 55.002, 55.003, 55.004, 55.005, 55.006, 55.007, 55.008, 55.009, 55.010, 55.011

*Phakopsora pachyrhizi*/Soybean/Leaf Disk Preventative (Soybean Rust)

Four-week old soybean plants are sprayed in a spray chamber with the formulated test compound diluted in water. Leaf disks are cut from treated plants and placed on agar into 24-well plates one day after application. Leaf disks are inoculated by spraying them with a spore suspension on their lower leaf surface. After an incubation period in a climate cabinet of 24-36 hours in darkness at 20° C. and 75% rh, the leaf disks are then kept at 20° C. with 12 h light/day and 75% rh. The percentage leaf disk area covered by disease is assessed when an appropriate level of disease appears on untreated check plants (12-14 days after application).

The following compounds gave at 200 ppm gave at least 80% disease control in this test when compared to untreated control leaf disks under the same conditions, which show extensive disease development:

55.001, 55.002, 55.003, 55.004, 55.005, 55.006, 55.007, 55.008, 55.009, 55.010, 55.011

What is claimed is:

1. A compound of formula (I)

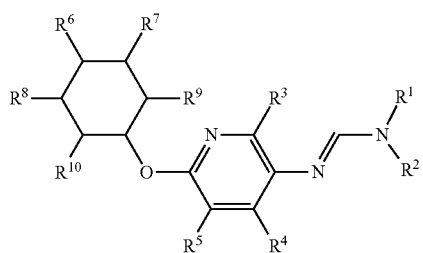

wherein
$R^1$ and $R^2$ independently represent hydrogen, $C_1$-$C_4$alkyl, $C_1$-$C_4$fluoroalkyl or $C_3$-$C_6$cycloalkyl; or $R^1$ and $R^2$ together with the nitrogen atom to which they are attached form a three to six-membered saturated cyclic group which may optionally contain one oxygen or one sulphur atom;

$R^3$ represents fluorine, chlorine, bromine, $C_1$-$C_4$ alkyl, $C_1$-$C_4$ alkenyl, $C_1$-$C_4$ haloalkyl, $C_1$-$C_4$ alkoxy or $C_3$-$C_6$ cycloalkyl;

$R^4$ represents hydrogen, halogen, cyano, hydroxy, formyl, carboxy, amino, $C_1$-$C_4$ alkyl, $C_2$-$C_6$ alkenyl, $C_2$-$C_6$ alkynl, $C_1$-$C_6$ haloalkyl, $C_1$-$C_6$ alkoxy or $C_3$-$C_6$ cycloalkyl;

$R^5$ represents hydrogen, halogen, cyano, $C_1$-$C_4$ alkyl, $C_1$-$C_4$ haloalkyl, $C_2$-$C_4$ alkynyl, $C_1$-$C_4$ alkoxy or $C_3$-$C_6$ cycloalkyl;

$R^6$, $R^7$, $R^8$, $R^9$ and $R^{10}$ independently represent hydrogen or $C_1$-$C_2$ fluoroalkoxy;

wherein at least one of $R^6$, $R^7$, $R^8$, $R^9$ and $R^{10}$ represent $C_1$-$C_2$ fluoroalkoxy;

or a tautomer, stereoisomer, enantiomer, salt or N-oxide thereof.

2. A compound of formula (I) according to claim 1 wherein
$R^1$ and $R^2$ independently represent hydrogen, $C_1$-$C_4$alkyl or cyclopropyl;
$R^3$ represents fluorine, chlorine, methyl, ethyl, ethenyl, propyl, propenyl, isopropyl, isopropenyl, cyclopropanyl, methoxy, ethoxy or $C_1$-$C_2$ fluoroalkyl;
$R^4$ represents hydrogen, halogen or $C_1$-$C_4$ alkyl;
$R^5$ represents hydrogen, halogen, cyano, $C_1$-$C_4$ alkyl, $C_1$-$C_4$ haloalkyl, cyclopropyl, ethynyl or $C_1$-$C_4$ alkoxy.

3. A compound of formula (I) according to claim 1 wherein
$R^1$ and $R^2$ independently represent hydrogen, methyl, ethyl, isopropyl, propyl or cyclopropyl;
$R^3$ represents methyl, ethyl, methoxy, fluorine and chlorine;
$R^4$ represents hydrogen, halogen or $C_1$-$C_4$ alkyl;
$R^5$ represents hydrogen, bromine, iodine, chlorine, cyano methyl, difluoromethyl, cyclopropyl, ethynyl or methoxy.

4. A compound of formula (I) according to claim 1 wherein
$R^1$ and $R^2$ independently represent hydrogen, methyl, ethyl, isopropyl, propyl or cyclopropyl;
$R^3$ represents methyl, methoxy, fluorine or chlorine;
$R^4$ represents hydrogen or $C_1$-$C_4$ alkyl;
$R^5$ represents hydrogen, bromine, iodine, chlorine, cyano, methyl or difluoromethyl.

5. A compound of formula (I) according to claim 1 wherein
$R^1$ represents methyl;
$R^2$ represents ethyl;
$R^3$ represents methyl, methoxy, fluorine or chlorine;
$R^4$ represents hydrogen;
$R^5$ represents hydrogen, bromine, cyano or methyl.

6. A compound of formula (I) according to claim 1 wherein $R^9$ and $R^{10}$ are hydrogen.

7. A compound of formula (I) according to claim 1 wherein $R^8$, $R^9$ and $R^{10}$ are hydrogen.

8. A compound of formula (I) according to claim 1 wherein $R^6$, $R^8$, $R^9$ and $R^{10}$ are hydrogen.

9. A compound of formula (I) according to claim 1 wherein $R^7$, $R^8$, $R^9$ and $R^{10}$ are hydrogen.

10. A composition comprising a fungicidally effective amount of a compound of formula (I) as defined in claim 1, optionally comprising at least one additional active ingredient.

11. A method of controlling or preventing phytopathogenic diseases on useful plants or on propagation material thereof, which comprises applying to the useful plants, the locus thereof or propagation material thereof a fungicidally effective amount of a compound of formula (I) as defined in claim 1.

* * * * *